(12) United States Patent
Lieberman

(10) Patent No.: US 7,396,360 B2
(45) Date of Patent: Jul. 8, 2008

(54) MINIMALLY INVASIVE METHOD AND APPARATUS FOR FUSING ADJACENT VERTEBRAE

(75) Inventor: Isador H. Lieberman, Pepper Pike, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 822 days.

(21) Appl. No.: 10/952,654

(22) Filed: Sep. 29, 2004

(65) Prior Publication Data

US 2006/0084977 A1   Apr. 20, 2006

(51) Int. Cl.
*A61B 17/70* (2006.01)
*A61B 17/88* (2006.01)
*A61B 17/58* (2006.01)
*A61B 17/90* (2006.01)
*A61F 2/44* (2006.01)

(52) U.S. Cl. .................. 606/247; 606/279; 606/104
(58) Field of Classification Search ............ 606/54, 606/57, 59, 61, 64, 72, 73, 86, 96–99, 102, 606/104
See application file for complete search history.

(56) References Cited

U.S. PATENT DOCUMENTS

| 1,201,864 A | 10/1916 | Overmeyer |
| 4,907,577 A * | 3/1990 | Wu ............................ 606/87 |
| 5,242,444 A * | 9/1993 | MacMillan .................. 606/61 |
| 5,746,741 A | 5/1998 | Kraus et al. |

(Continued)

FOREIGN PATENT DOCUMENTS

| CH | 692 023 A5 | 1/2002 |
| EP | 940124 A1 * | 9/1999 |
| EP | 1 273 272 A2 | 1/2003 |

OTHER PUBLICATIONS

Grob et al. (1998) Translaminar Screw Fixation in the Lumbar Spine: Technique, Indications, Results, Eur. Spine J. 7:178-186.

(Continued)

*Primary Examiner*—Eduardo C. Robert
*Assistant Examiner*—Jay R Sigler
(74) *Attorney, Agent, or Firm*—Tarolli, Sundheim, Covell & Tummino LLP

(57) ABSTRACT

The present invention is a minimally invasive surgical method for fusing adjacent vertebrae. A first K-wire is inserted into the spinous process of an upper vertebrae. A second K-wire is inserted into a transverse process of a lower vertebrae. A first fixation block is secured to the first K-wire and a second fixation block is secured to the second K-wire. A rod member extends across the K-wires. A swivel block assembly is secured to achieve a desired angle for a first axis along which a first screw will be implanted into a facet joint. The swivel block assembly is secured at a desired axial position on the rod member. Percutaneous access to the upper vertebrae along the first axis is then obtained via a cannula. A removable screw having a threaded section for implantation across the facet joint and an elongated shank section that is shearable subcutaneously is inserted through the cannula. The threaded section is implanted along the first axis across the facet joint to attach the upper and lower vertebrae. A shearing tool is inserted percutaneously over the shank section and the shank section is sheared off immediately above the lamina.

12 Claims, 28 Drawing Sheets

U.S. PATENT DOCUMENTS

| | | |
|---|---|---|
| 6,287,313 B1 | 9/2001 | Sasso |
| 6,485,518 B1 * | 11/2002 | Cornwall et al. ......... 623/17.11 |
| 6,530,930 B1 | 3/2003 | Marino et al. |
| 6,547,795 B2 | 4/2003 | Schneiderman |
| 6,562,046 B2 | 5/2003 | Sasso |
| 6,669,698 B1 | 12/2003 | Tromanhauser et al. |
| 7,147,640 B2 * | 12/2006 | Huebner et al. ............... 606/59 |
| 2002/0007188 A1 | 1/2002 | Arambula et al. |
| 2005/0080428 A1 * | 4/2005 | White ........................ 606/102 |
| 2005/0209694 A1 * | 9/2005 | Loeb ....................... 623/17.11 |

OTHER PUBLICATIONS

Jang et al., (2003) Guide Device for Percutaneous Placement of Translaminar Facet Screws After Anterior Lumbar Interbody Fusion, J. Neurosurg (Spine 1) 98:100-103.

* cited by examiner

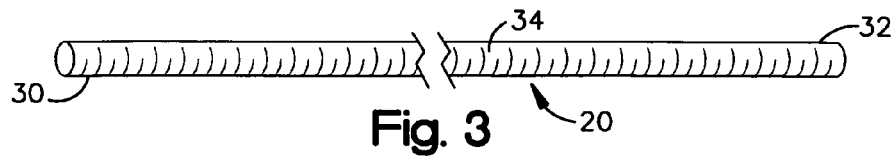
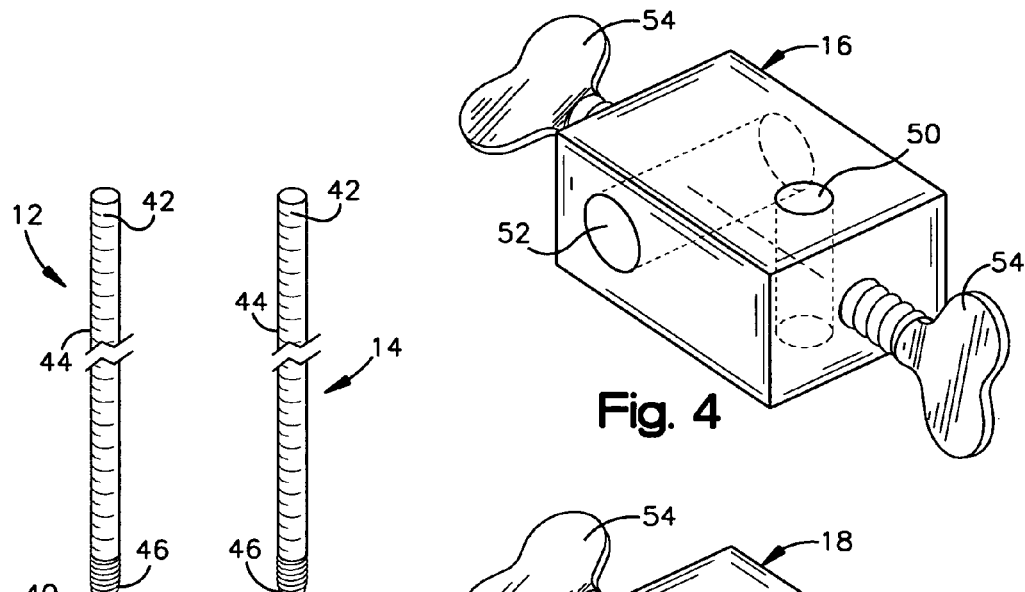
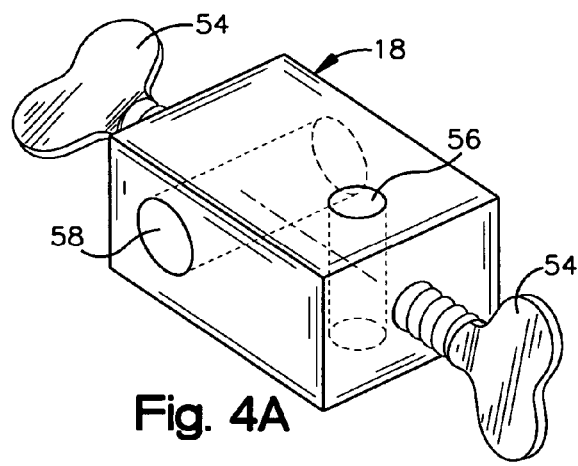
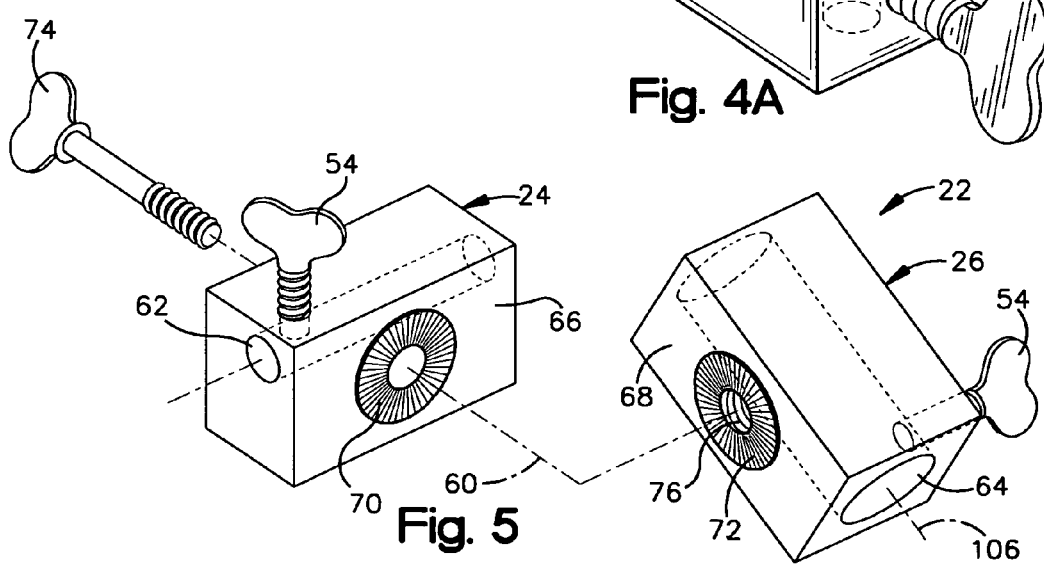

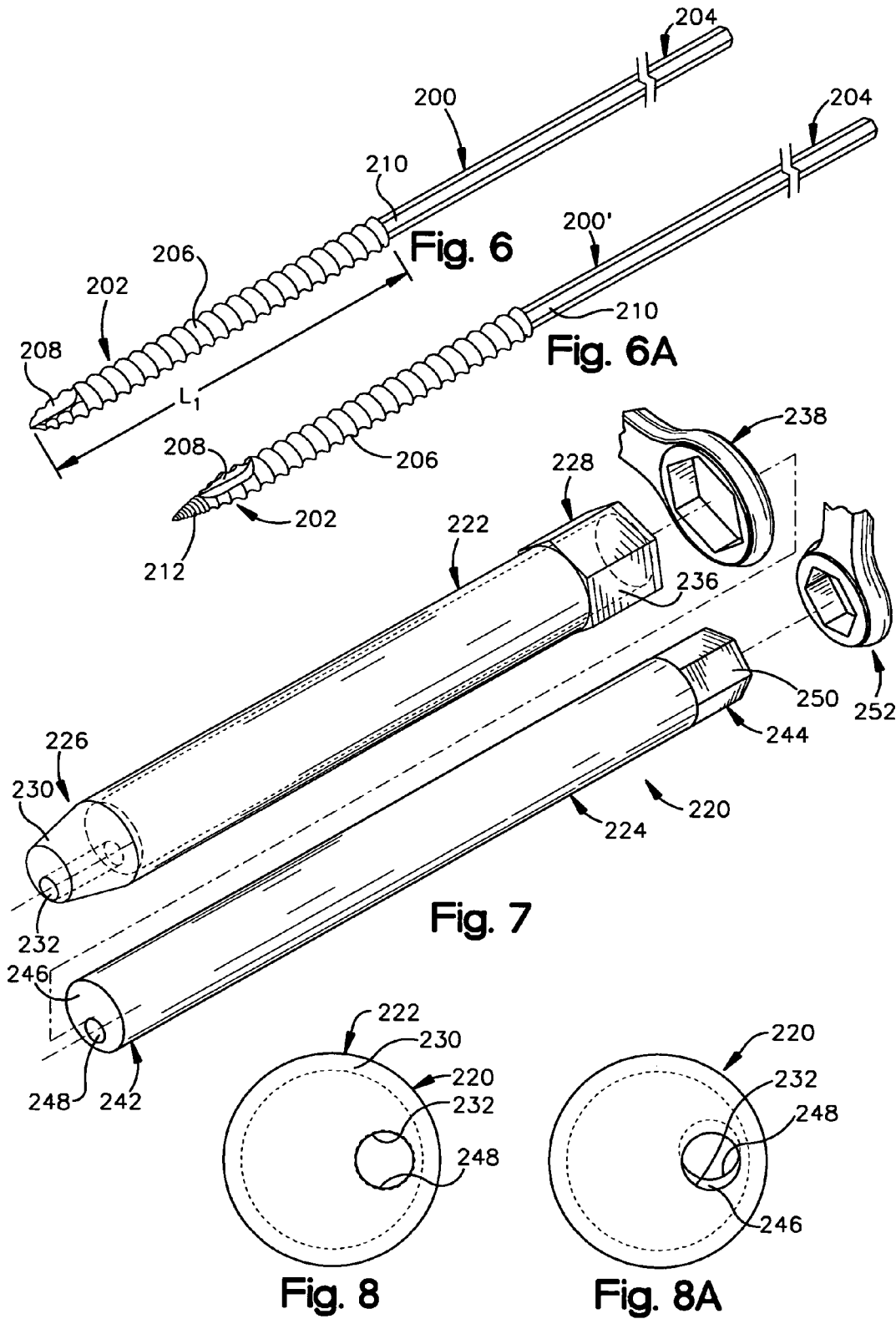

MINIMALLY INVASIVE METHOD AND APPARATUS FOR FUSING ADJACENT VERTEBRAE

TECHNICAL FIELD

The present invention relates to a minimally invasive method and apparatus for fusing adjacent vertebrae.

BACKGROUND OF THE INVENTION

Over 200,000 spinal fixation and spinal fusion procedures are performed annually to correct various congenital and degenerative spinal disorders in humans. Many of these corrective surgical procedures are performed in the lumbar and lumbosacral regions of the spine where traumatic and age-related disc degeneration is common. One such procedure involves the implantation of spinal fixation instrumentation, including plates and rods, using pedicle screws. Another procedure involves the implantation of one or more anterior fusion cages into the intervertebral disc space following a discectomy. These and other known spinal fixation and/or fusion procedures can be quite invasive, traumatic, and time consuming. Further, problems with post-operative stability and pseudoarthrosis are often associated with many of these procedures.

It is well known that the two facet joints, which are formed between each pair of adjacent vertebrae, share and support the axial load on the spine with a respective intervertebral disc. Accordingly, it has been suggested to place screws either directly across the facet joints of adjacent vertebrae or indirectly across the facet joints through the lamina (i.e. translaminar) as both a primary means for spinal fixation and as a secondary means for fixation to augment anterior fusion or pedicle screw fixation instrumentation. Indeed, this suggestion has been accepted by many surgeons as facet screws (direct and translaminar) are now being implanted on a regular basis. In order to further improve upon the use of such facet screws, a minimally invasive method and apparatus for accurately and repeatably placing facet screws across the facet joints and fusing adjacent vertebrae is needed.

SUMMARY OF THE INVENTION

The present invention is a minimally invasive surgical method for fusing adjacent upper and lower vertebrae. The method utilizes an apparatus comprising first and second K-wires, first and second fixation blocks, a swivel block having relatively movable first and second block members, a rod member extending between the fixation blocks and the first block member, and a cannula extending from the second block member. The first K-wire is inserted into the center of the spinous process of the upper vertebrae. The second K-wire is inserted into a transverse process on a first side of the lower vertebrae. The first fixation block is secured to the first K-wire and the second fixation block is secured to the second K-wire with the rod member extending across the K-wires. The second block member of the swivel block assembly is secured relative to the first block member to achieve a desired angle for a first axis along which a first screw will be implanted into the facet joint on the first side. The swivel block assembly is secured at a desired axial position on the rod member. Percutaneous access to the second side of the upper vertebrae along the first axis is then obtained via the cannula. A first removable screw is provided for insertion into the cannula. The first screw has a threaded section for implantation across the facet joint to promote fusion of the adjacent vertebrae and an elongated shank section that is shearable subcutaneously following implantation. The first screw is inserted through the cannula and the threaded section is implanted along the first axis across the facet joint on the first side to attach the upper and lower vertebrae. A shearing tool is inserted percutaneously over the elongated shank section of the first screw and the shank section is sheared off to form an accessible head portion of the shank section that lies immediately above the surface of the lamina of the upper vertebrae.

In accordance with a further aspect of the inventive method, a burring bit is inserted into the cannula and used to burr the articular surfaces of the facet joint on the second side to widen the facet joint for accepting a bone graft material.

In accordance with additional aspects of the inventive method, wherein prior to said step of securing the second block member of the swivel block assembly relative to the first block member to achieve a desired angle for the first axis, the cannula is moved to aim the cannula toward the facet joint on the second side of the vertebrae along a second axis. Percutaneous access along the second axis is then obtained to the facet joint on the second side via the cannula and a bone graft material is placed into the facet joint on the second side through the cannula to assist with fusion of the upper and lower vertebrae.

In accordance with still other aspects of the inventive method, the cannula is removed from percutaneous insertion and the second K-wire is removed from the transverse process on the first side of the lower vertebrae. The second K-wire is then inserted into the transverse process on the second side of the lower vertebrae. The second fixation block is then secured to the second K-wire. Next, the first fixation block is released from the first K-wire and is rotated with the rod member extending across the K-wires. The first fixation block is secured to the first K-wire. The second block member of the swivel block assembly is then secured relative to the first block member to achieve a desired angle for a third axis along which a second screw will be implanted into the facet joint on the second side. The swivel block assembly is secured at a desired axial position along the rod member. Percutaneous access to the first side of the upper vertebrae is obtained via the cannula. A second removable screw is provided for insertion into the cannula. The second screw has a threaded section for implantation across the facet joint to promote fusion of the adjacent vertebrae and an elongated shank section that is shearable subcutaneously following implantation. The second screw is inserted through the cannula and implanted along the third axis across the facet joint on the second side to attach the upper and lower vertebrae. The shearing tool is inserted percutaneously over the elongated shank section of the second screw and the shank section is sheared off to form an accessible head portion of the shank section that lies above the surface of the lamina of the upper vertebrae.

In accordance with additional aspects of the inventive method, the cannula is moved to aim the cannula along a fourth axis toward the facet joint on the first side previously secured with the first screw. Percutaneous access to the facet joint on the first side is obtained via the cannula and a bone graft material is placed through the cannula into the facet joint around the previously implanted first screw to assist with fusion of the upper and lower vertebrae.

In accordance with additional aspects of the inventive method, the step of securing the second block member of the swivel block assembly relative to the first block member to achieve the desired angle for the first axis along which the first screw is implanted includes calculating the desired angle for the centerline of the cannula to extend from the second side of the vertebrae toward the facet joint on the first side along the first axis.

In accordance with additional aspects of the inventive method, the step of securing the second block member of the swivel block assembly relative to the first block member to achieve the desired angle for the third axis along which the second screw is implanted includes calculating the desired angle for the centerline of the cannula to extend from the first side of the vertebrae toward the facet joint on the second side along the third axis.

In accordance with additional aspects of the inventive method, the step of securing the swivel block assembly at a desired axial position on the rod member includes the step of calculating the desired axial position for the swivel block assembly along the rod member.

The present invention further provides an apparatus for fusing a facet joint between adjacent vertebrae in a minimally invasive surgical procedure. The apparatus includes a first K-wire for inserting into one of the adjacent vertebrae, a first fixation block removably connected to the first K-wire, a second K-wire for inserting into the other vertebrae, a second fixation block removably connected to the second K-wire, a rod member removably connected to both of the first and second fixation blocks, and a swivel block assembly comprising relatively movable first and second block members. The rod member is removably connected to the first block member. A cannula provides percutaneous access to the vertebrae and extends from the second block member. A removable screw having a threaded section for implantation across the facet joint to promote fusion of the adjacent vertebrae and an elongated shank section that is shearable subcutaneously following implantation is inserted through the cannula.

In accordance with one aspect of the invention, each of the first and second K-wires includes means for measuring axial length along the K-wires.

In accordance with another aspect of the invention, the rod member includes means for measuring axial length along the rod member.

In accordance with another aspect of the invention, the swivel block assembly includes positioning means for controllably adjusting the angular position of the first and second block members relative to each other.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 2 is a perspective view of a component of the apparatus of FIG. 1;

FIG. 2A is a perspective view of a component of the apparatus of FIG. 1;

FIG. 3 is a perspective view of another component of the apparatus of FIG. 1;

FIG. 4 is a perspective view of another component of the apparatus of FIG. 1;

FIG. 4A is a perspective view of another component of the apparatus of FIG. 1;

FIG. 5 is an exploded perspective view of another component of the apparatus of FIG. 1;

FIG. 6 is a perspective view of a screw to be implanted in accordance with the present invention;

FIG. 6A is a perspective view of an alternate screw to be implanted in accordance with the present invention;

FIG. 7 is an exploded perspective view of a tool for use with the present invention;

FIG. 8 is an end view of the tool of FIG. 7;

FIG. 8A is a view similar to FIG. 8 illustrating parts of the tool in different positions;

DESCRIPTION OF EMBODIMENTS

Figure 1:
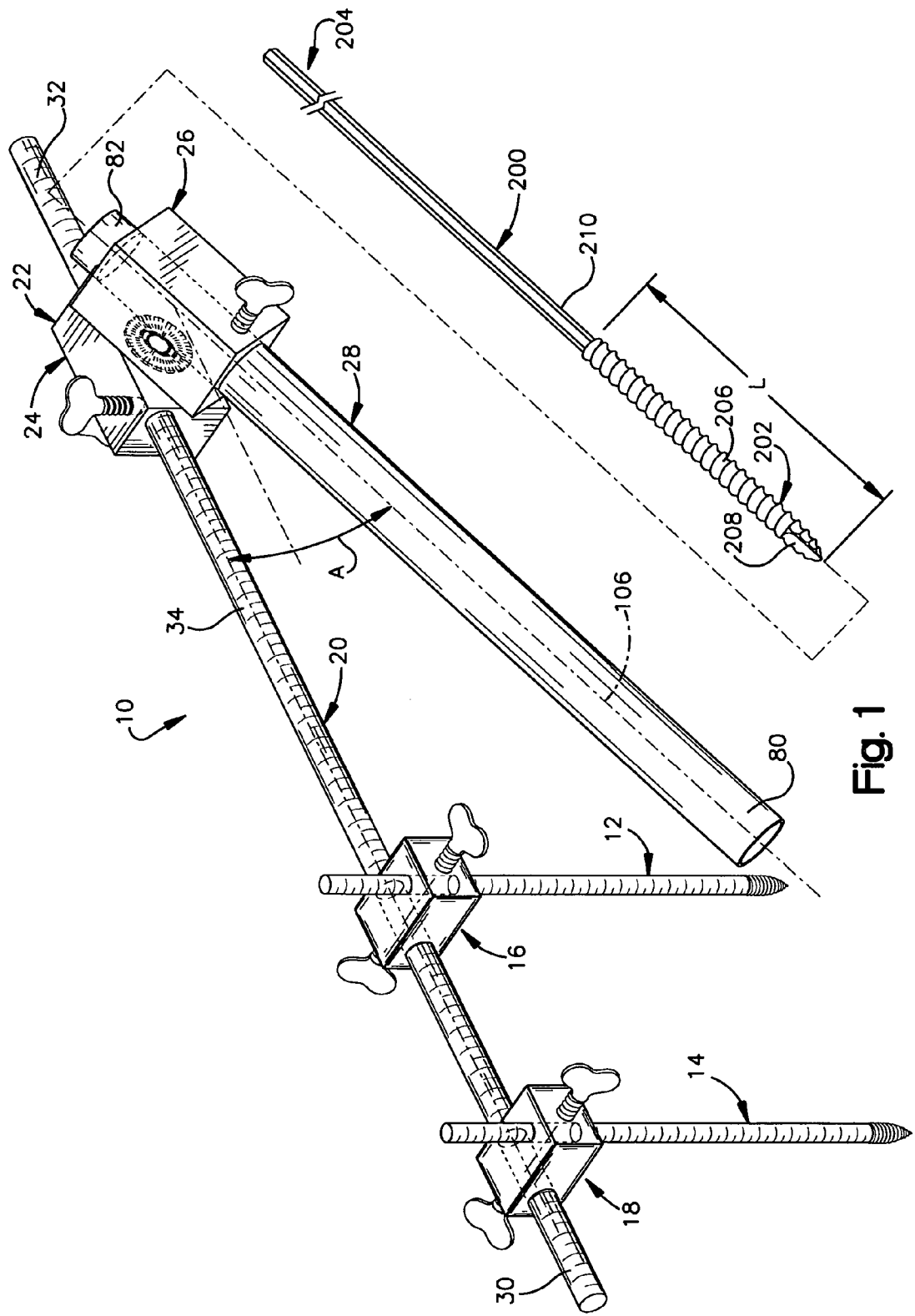
FIG. 1 is a perspective view of an apparatus for placing facet screws in accordance with the present invention.

The present invention relates to a minimally invasive method and apparatus for fusing adjacent vertebrae. As representative of the present invention, FIG. 1 illustrates an apparatus 10 comprising first and second Kirschner wires 12 and 14 (commonly referred to as "K-wires"), first and second fixation blocks 16 and 18, a rod member 20, a swivel block assembly 22 comprising first and second block members 24 and 26, a cannula 28, and at least one removable screw 200.

As may be seen in FIG. 3, the rod member 20 is a cylindrical component that may be hollow or solid and is made from any suitable metal or plastic. The rod member 20 has oppositely disposed first and second ends 30 and 32 and an outer diameter of 4 to 7 mm. The rod member 20 includes an outer surface 34 with graduations for measuring axial distances along its length. It is contemplated that other means for measuring axial length along the rod member 20 could also be used.

The first and second K-wires 12 and 14 (FIG. 2) are identical parts, although it should be understood that the K-wires could have different sizes or shapes. Each of the first and second K-wires 12 and 14 is an elongate rod made of a biocompatible metal or other suitable material with an outer diameter of 2 to 4 mm. As shown in FIGS. 2 and 2A, each K-wire 12 and 14 has oppositely disposed distal and proximal ends 40 and 42 and a cylindrical outer surface 44 extending between the ends. The distal end 40 of each of the K-wires 12 and 14 includes self-tapping threads 46. The cylindrical outer surface 44 of each of the K-wires 12 and 14 includes graduations for measuring axial lengths along each K-wire. It is contemplated that other means for measuring axial length along the K-wires 12 and 14 could also be used.

The first and second fixation blocks 16 and 18 (FIGS. 4 and 4A) are also identical components, although it should be understood that certain aspects of the fixation blocks need not be identical. Each of the first and second fixation blocks 16 and 18 is a generally rectangular part made of any suitable metal or plastic. The first fixation block 16 (FIG. 4) includes perpendicularly extending first and second passages 50 and 52. As shown in FIG. 3, the first and second passages 50 and 52 are offset from each other by a predetermined amount and thus do not intersect. In the assembled condition of FIG. 1, the first K-wire 12 extends into the first passage 50 in the first fixation block 16 and the rod member 20 extends into the second passage 52.

The first fixation block 16 further includes threaded fasteners in the form of thumbscrews 54 that extend into the first and second passages 50 and 52 for securing the first K-wire 12 and the rod member 20 in the first and second passages, respectively. It should be understood, however, that other suitable means for securing the first K-wire 12 and the rod member 20 to the first fixation block 16, such as clamps, latches, ratchet mechanisms, etc., could also be used, and that the securing means could be positioned on the exterior of the first fixation block.

In an identical fashion to the first fixation block 16, the second fixation block 18 includes perpendicularly extending first and second passages 56 and 58 that are offset from each other by a predetermined amount and thus do not intersect. The predetermined amount of offset between the first and second passages 56 and 58 in the second fixation block 18 is the same as the predetermined amount of offset between the first and second passages 50 and 52 in the first fixation block 16. In the assembled condition of FIG. 1, the second K-wire 14 extends into the first passage 56 in the second fixation block 18 and the rod member 20 extends into the second passage 58.

The second fixation block 18 further includes threaded fasteners in the form of thumbscrews 54 that extend into the first and second passages 56 and 58 for securing the second K-wire 14 and the rod member 20 in the first and second passages 56 and 58, respectively. It should be understood, however, that other suitable means for securing the second K-wire 14 and the rod member 20 to the second fixation block 18, such as clamps, latches, ratchet mechanisms, etc., could also be used, and that the securing means could be positioned on the exterior of the second fixation block.

As shown in FIG. 5, the first and second block members 24 and 26 of the swivel block assembly 22 are movable relative to each other about an axis 60. Each of the first and second block members 24 and 26 is a generally rectangular part made of any suitable metal or plastic. The first block member 24 includes a passage 62 for receiving the rod member 20. A threaded fastener in the form of a thumbscrew 54 extends into the passage 62 for securing the rod member 20 in the passage. The second block member 26 further includes a passage 64 for receiving the cannula 28. The passage 64 has a centerline 106 that becomes the centerline of the cannula 28 when the cannula is positioned within the passage. A threaded fastener in the form of a thumbscrew 54 extends into the passage 64 for securing the cannula 28 in the passage. It should be understood, however, that other suitable means for securing the rod member 20 and the cannula 28 to the swivel block assembly 22, such as clamps, latches, ratchet mechanisms, etc., could also be used, and that these securing means could be positioned on the exterior of the swivel block assembly.

The first and second block members 24 and 26 further include abutting surfaces 66 and 68, respectively, with means for controllably adjusting the angular position of the block members relative to each other. In accordance with the illustrated embodiment of the invention, this is accomplished via a first ring of radially extending serrations 70 on the surface 66 of the first block member 24 that is centered on the axis 60 and engaged with a second ring of radially extending serrations 72 on the surface 68 of the second block member 26 that is also centered on the axis 60. A threaded fastener in the form of a thumbscrew 74 extends through the first block member 24 and into a threaded opening 76 in the second block member 26 along the axis 60 for securing the block members in a desired relative angular position. It should be understood, however, that other suitable means for securing the block members 24 and 26 in a desired angular position could be used, and that the securing means could be located elsewhere on the block members. Further, it should also be understood that other suitable means for controllably adjusting the relative angular position of the first and second block members 24 and 26 could be employed.

The cannula 28 (FIG. 1) is a thin-walled hollow cylinder made of a biocompatible metal or other suitable material and has oppositely disposed distal and proximal ends 80 and 82. In accordance with one embodiment of the present invention, the cannula 28 has an outer diameter of about 4.5 mm and an inner diameter of about 4.3 mm, although it should be understood that these dimensions may be varied between 4 and 6 mm for the outer diameter and 3.5 to 5 mm for the inner diameter.

FIG. 6 illustrates a first embodiment of the screw 200 to be implanted in accordance with the present invention. The screw 200 has oppositely disposed distal and proximal ends 202 and 204 and is made of a biocompatible material, such as titanium. The distal end 202 of the screw 200 includes a threaded section 206 that has a self-tapping feature 208 as is known in the art. In accordance with one embodiment, the threaded section 206 of the screw 200 has a major diameter of 4.3 mm and a minor diameter of 3.8 mm, but it should be understood that these dimensions can be varied based on the pathology and surgical needs. The length L of the threaded section 206 of the screw 200 may be determined during surgery as discussed below.

The screw 200 further includes an elongated shearable section 210 that extends from the threaded section 206 to the proximal end 204. As illustrated in FIG. 6, the shearable section 210 has a hexagonal shape in cross-section. It should be understood, however, that the shearable section 210 could have another suitable cross-sectional shape. The shearable section is 3 to 3.5 mm in diameter (across the hexagonal shape), and is thus smaller in diameter than the minor diameter of the threaded section 206.

FIG. 6A illustrates a screw 200' in accordance with an alternate embodiment. The screw 200' has all of the same features as the screw 200', but further includes a drill tip 212 built into the threaded section 206 at the distal end 202. The drill tip 212 is sharply pointed and aids in getting the threaded section 206 of the screw 200' started when screwing into bone, particularly when no pilot hole for the screw is drilled in the bone.

FIGS. 7, 8 and 8A illustrate a tool 220 for shearing the screws 200 and 200'. The tool 220 comprises relatively movable first and second sleeves 222 and 224. The first and second sleeves 222 and 224 are generally cylindrical in shape and the second sleeve is disposed coaxially within the first sleeve. The first sleeve 222 has oppositely disposed distal and proximal ends 226 and 228. The distal end 226 includes a tapered nose section 230 having a predetermined axial length and an axially extending passage 232 that is offset from the centerline of the first sleeve 222. The proximal end 228 of the first sleeve 222 includes a hexagonal outer surface 236 that is engageable by a first wrench 238.

The second sleeve 224 has oppositely disposed distal and proximal ends 242 and 244. The distal end 242 of the second sleeve 224 includes an end plate 246 with a shearing aperture 248 that is offset from the centerline of the second sleeve and which is alignable with the passage 232 in the distal end 226 of the first sleeve 222. The proximal end 244 of the second sleeve 224 extends axially beyond the proximal end 228 of the first sleeve 222 includes a hexagonal outer surface 250 that is engageable by a second wrench 252. The first and second sleeves 222 and 224 are rotatable relative to each other by rotation of the wrenches 238 and 252 to align (FIG. 8) or misalign (FIG. 8A) the passage 232 with the shearing aperture 248.

Figure 9:
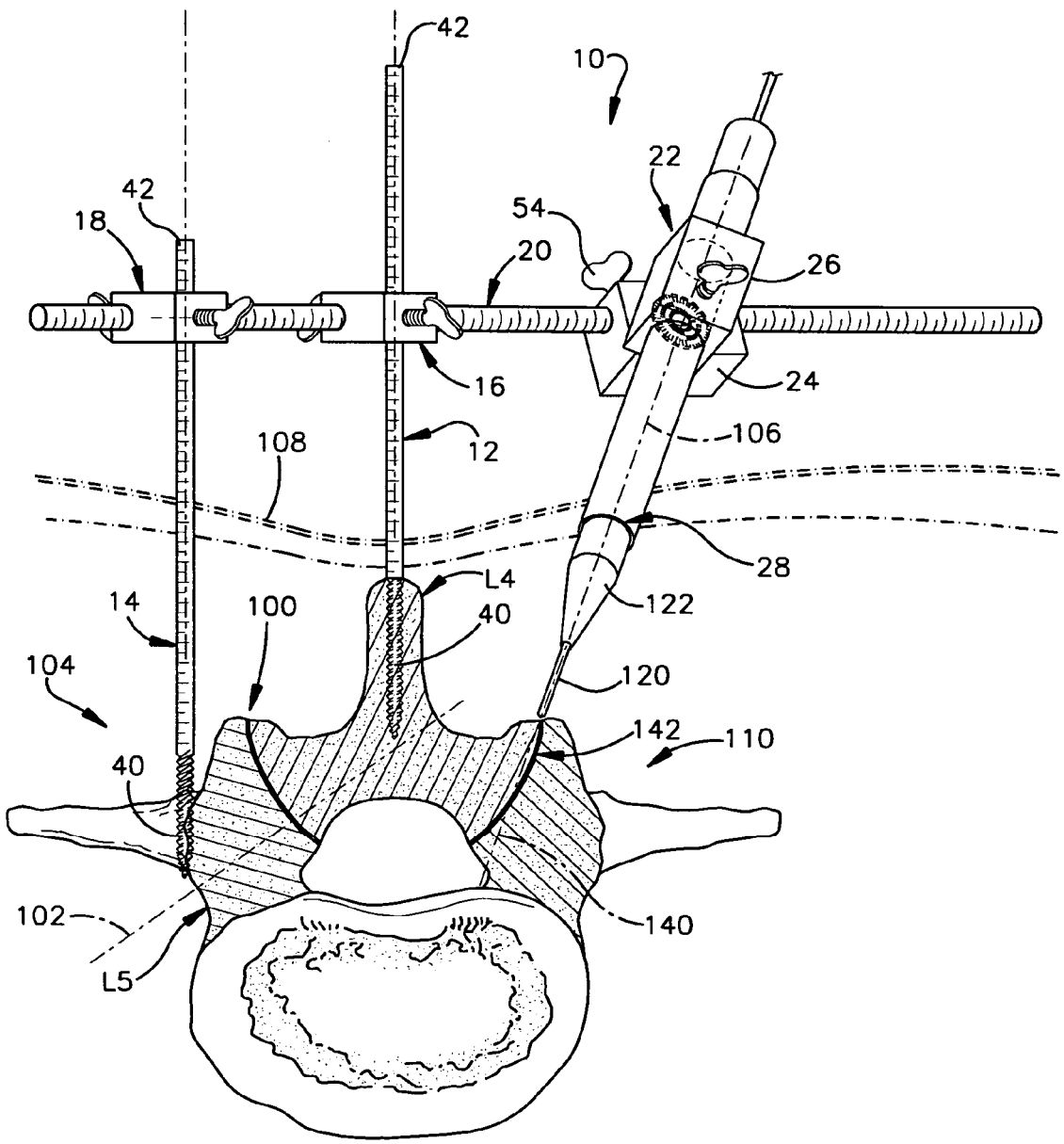
FIG. 9 is a schematic view of adjacent lumbar vertebrae in the transverse plane and illustrating components of the apparatus of FIG. 1 at an early stage of the inventive method.
Figure 10:
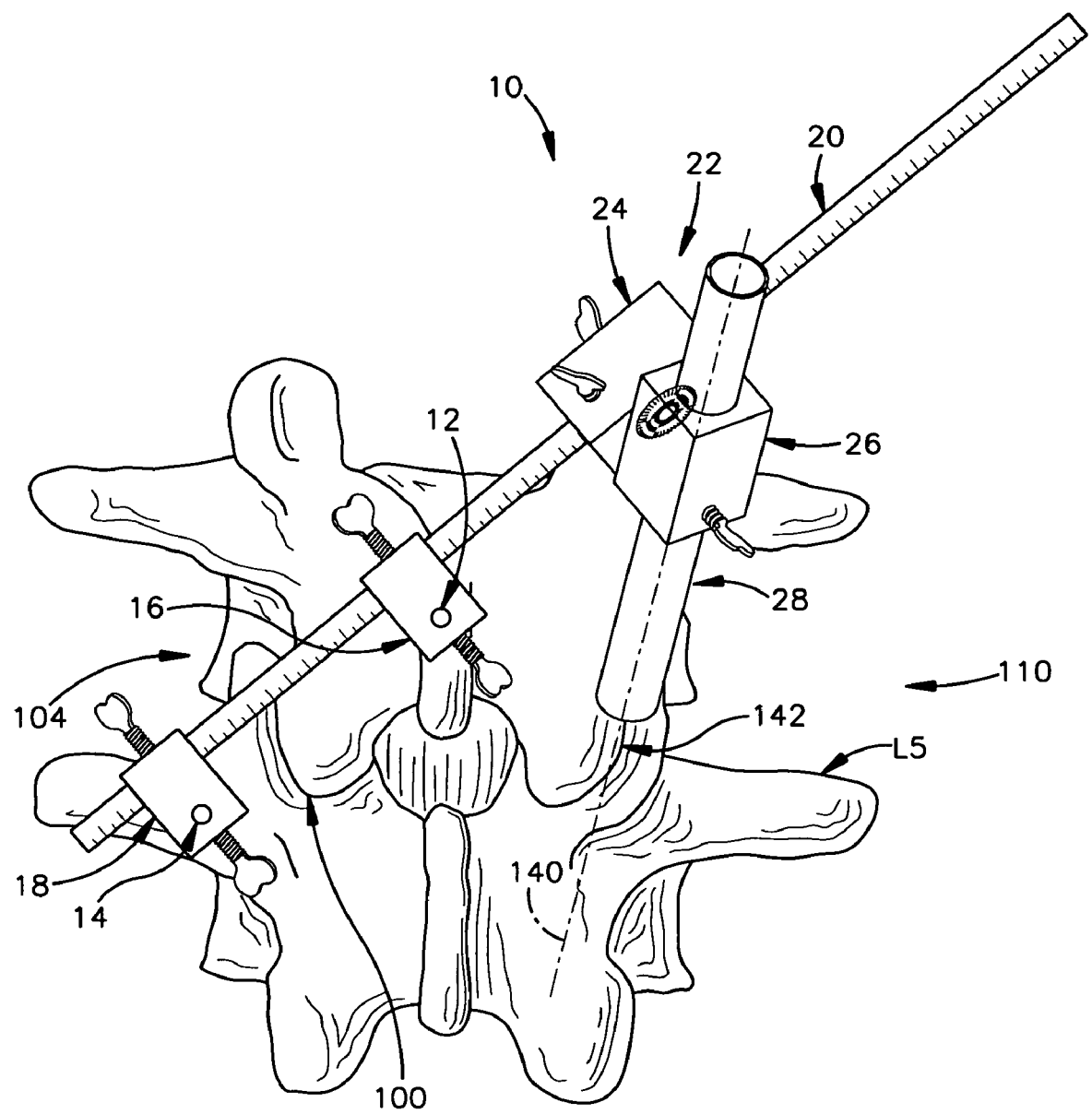
FIG. 10 is a schematic posterior view of the apparatus at a subsequent stage to that of FIG. 7.
Figure 15:
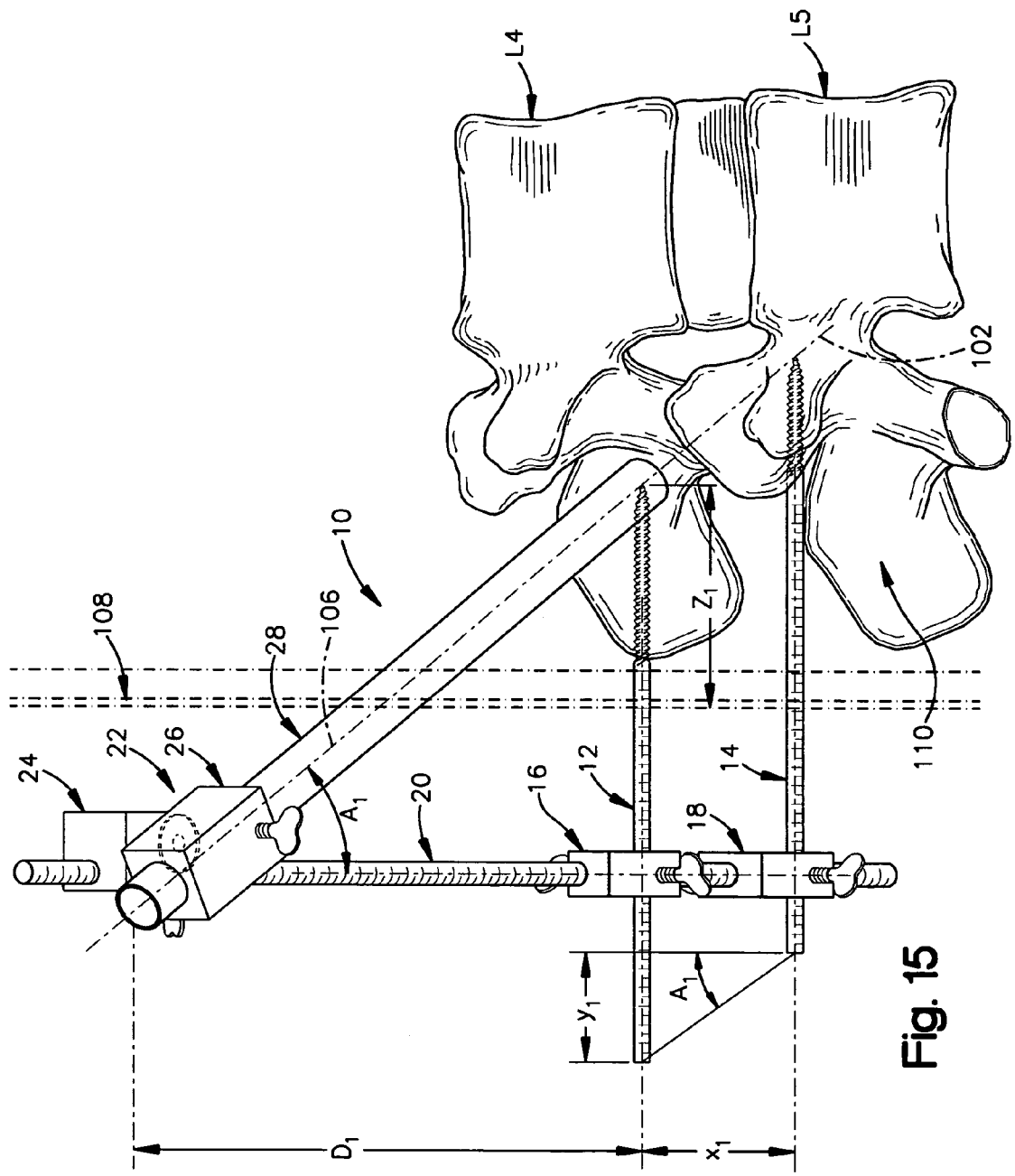
FIG. 15 is a schematic side view of the apparatus of FIG. 14.

To use the apparatus 10 to fuse adjacent vertebrae, such as the L4 and L5 vertebrae shown in FIGS. 9, 10 and 15, in a minimally invasive procedure, the patient is placed in the prone position and X-ray imaging equipment is set-up to provide views in both the antero-posterior (AP) plane and the lateral plane so that the procedure can be performed under fluoroscopic guidance. It should be understood to those skilled in the art that other known navigation assistance devices and equipment could alternatively be used. A stab incision is then made through the skin and the first K-wire 12 is inserted through the incision and into the center of the spinous process of the L4 vertebrae. As may be seen in FIGS. 9 and 15, the distal end 40 of the first K-wire 12 is screwed into the spinous process until the distal tip reaches a point along an axis 102 on which a first screw 200 is to be inserted.

Next, through another percutaneous stab incision, the second K-wire 14 is inserted into the transverse process on a first side 104 (the left side as viewed in FIG. 9) of the L5 vertebrae and extends in parallel with the first K-wire 12 in both the sagittal and coronal planes as shown in FIGS. 9, 10 and 15. The distal end 40 of the second K-wire 12 is screwed into the transverse process just lateral to the facet joint 100 on the first side 104 of the vertebrae up to the junction of the transverse process and the pedicle on the first side.

The first fixation block 16 is then slid onto the first K-wire 12, with the first K-wire extending into the first passage 50 in the first fixation block. Similarly, the second fixation block 18 is slid onto the second K-wire 14 with the second K-wire extending into the first passage 56 in the second fixation block. The first end 30 of the rod member 20 is slid then into the second passages 52 and 58 in the first and second fixation blocks 16 and 18, respectively, so that it extends across the first and second K-wires 12 and 14. The thumbscrews 54 that extend into the second passages 52 and 58 are tightened to secure the rod member 20 to the fixation blocks 16 and 18.

Next, the swivel block assembly 22 is slid onto the second end 32 of the rod member 20, which is projecting out over a second side 110 (or right side as viewed in FIG. 9) of the L4 and L5 vertebrae, with the rod member 20 extending through the passage 62 in the first block member 24. The second block member 26 is rotated about the axis 60 to aim the centerline 106 of the passage 64 along an axis 140 that extends toward a facet joint 142 on the second side 110 of the vertebrae.

Figure 11:
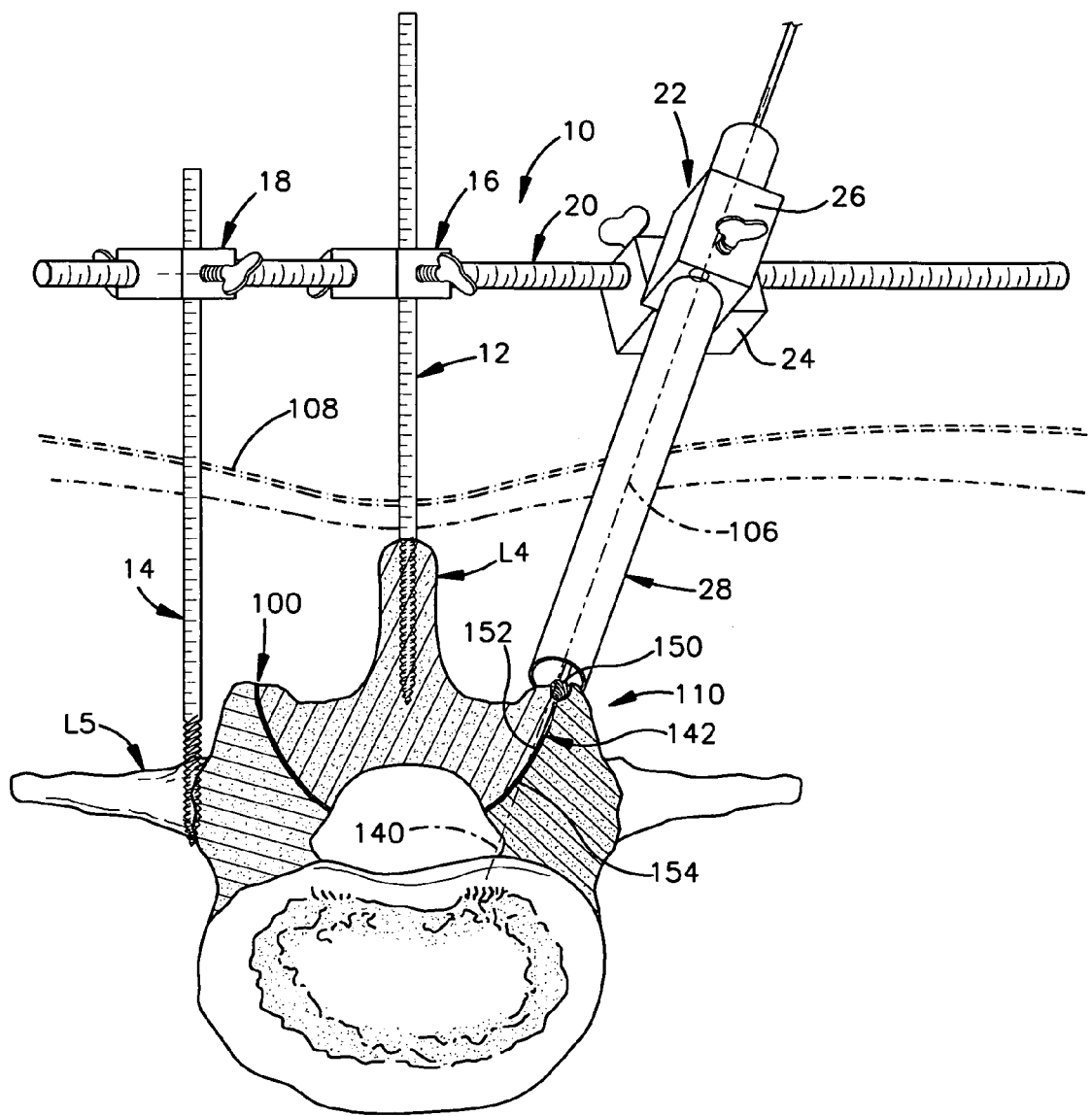
FIGS. 11-13 are views similar to FIG. 9 illustrating various steps according to the inventive method.

A scalpel (not shown) is used to incise the skin 108 on the second side 110 of the vertebrae to accept the cannula 28. With the cannula 28 temporarily removed, the incision is made using the passage 64 through the second block member 24 of the swivel block assembly 22 to orient the incision along the proper axes 106 and 140. Under fluoroscopic guidance, a guidewire 120 is passed through the incision along the axes 106 and 140 to the surface of the facet joint 142 on the second side 110 of the L4 and L5 vertebrae under fluoroscopic guidance. Next, a blunt obturator 122 is passed over the guidewire 120 to create subcutaneous space for the cannula 28 along the axis 140. The cannula 28, which is guided for movement along the axes 106 and 140 by virtue of the passage 64 through the second block member 26, is then passed over the obturator 122 and the guidewire 120. The cannula 28 is moved along the axes 106 and 140 until the distal end of the cannula 28 docks against the surface of the facet joint 142 as shown in FIGS. 10 and 11. The guidewire 120 and the obturator 122 are then removed from the cannula 28.

After ensuring that all of the thumbscrews 54 and 74 are secure and that the alignment of the axis 140 is correct, a burring bit 150 (FIG. 11) is inserted into the cannula. The burring bit 150 is rotated by a drill (not shown) to burr the opposing surfaces 152 and 154 of the inferior articular process and the superior articular process on the second side 110 of the L4 and L5 vertebrae, respectively. Burring these surfaces 152 and 154 widens the facet joint so that a bone graft material is more easily placed into the facet joint 142. It is contemplated that the cannula 28 may be moved slightly along the facet joint 142 during the burring process in order to access a larger area of the facet joint with the burring bit 150.

Figure 12:
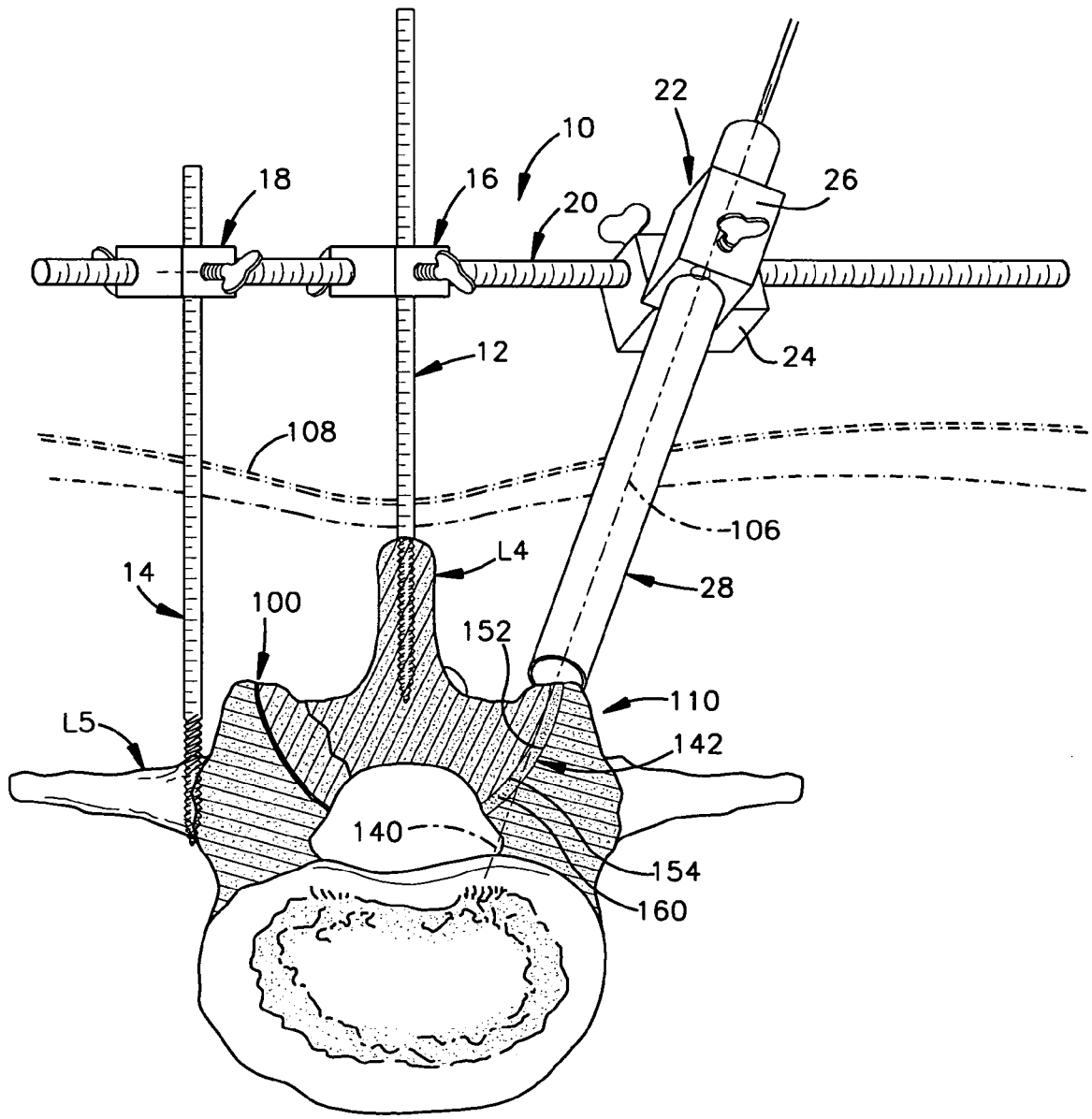

After the articular surfaces 152 and 154 of the facet joint 142 on the second side 110 of the L4 and L5 vertebrae have been burred out, a bone graft (or bone substitute) material 160 (FIG. 12) for helping to fuse the L4 and L5 vertebrae is placed into the facet joint 142 through the cannula 28. The bone graft material 160 may be fed into the facet joint 142 using any known suitable instrument(s). With the bone graft material 160 placed in the facet joint 142, the cannula 28 is removed from the skin 108 and the thumbscrew 74 is released to allow relative movement of the first and second block members 24 and 26.

Next, the cannula 28 will be oriented along the axis 102 for implantation of the first screw 200 across the facet joint 100 on the first side 104 of the vertebrae. In order to aim the cannula 28 toward the facet joint 100, the other thumbscrews 54 may also be released to allow additional movement of the swivel block assembly 22. Releasing the other thumbscrews 22 may allow the cannula 28 to be positioned over the existing incision through the skin 108 while being aimed toward the facet joint 100 along the axis 102 so that the same incision can be utilized again.

According to the inventive method, the next steps involve calculations to determine the following three parameters: (1) the length $L_1$ (FIG. 6) of the threaded section 206 of the screw 200 to be implanted; (2) the desired angle $A_1$ (FIG. 13) for the cannula 28 to extend from the swivel block assembly 22, which provides the trajectory for the implantation of the first screw 200 across the facet joint 100 on the first side 104; and (3) the desired axial position $D_1$ for the swivel block assembly 22 along the rod member 20. As will be seen in the calculations set forth below, the apparatus 10 according to the present invention utilizes the position and relationship of the first and second K-wires 12 and 14 to determine the entry point and trajectory upon which the screw 200 is implanted into the L4 and L5 vertebrae.

The length $L_1$ of the threaded section 206 is determined by measuring the axial difference $X_1$ between the two identical K-wires 12 and 14 and measuring the horizontal difference $Y_1$ between the two K-wires. The graduations on the K-wires 12 and 14 and/or another suitable means can assist in taking these measurements. The length $L_1$ is calculated with the following equation: $L_1 = \sqrt{(X_1^2 + Y_1^2)}$. Use of this equation to determine the desired screw length $L_1$ helps to ensure that the threaded section 206 of the screw 200, when implanted across the facet joint 100, will not extend beyond the cortex of the superior articular process where nerve damage could become an issue.

Figure 13:
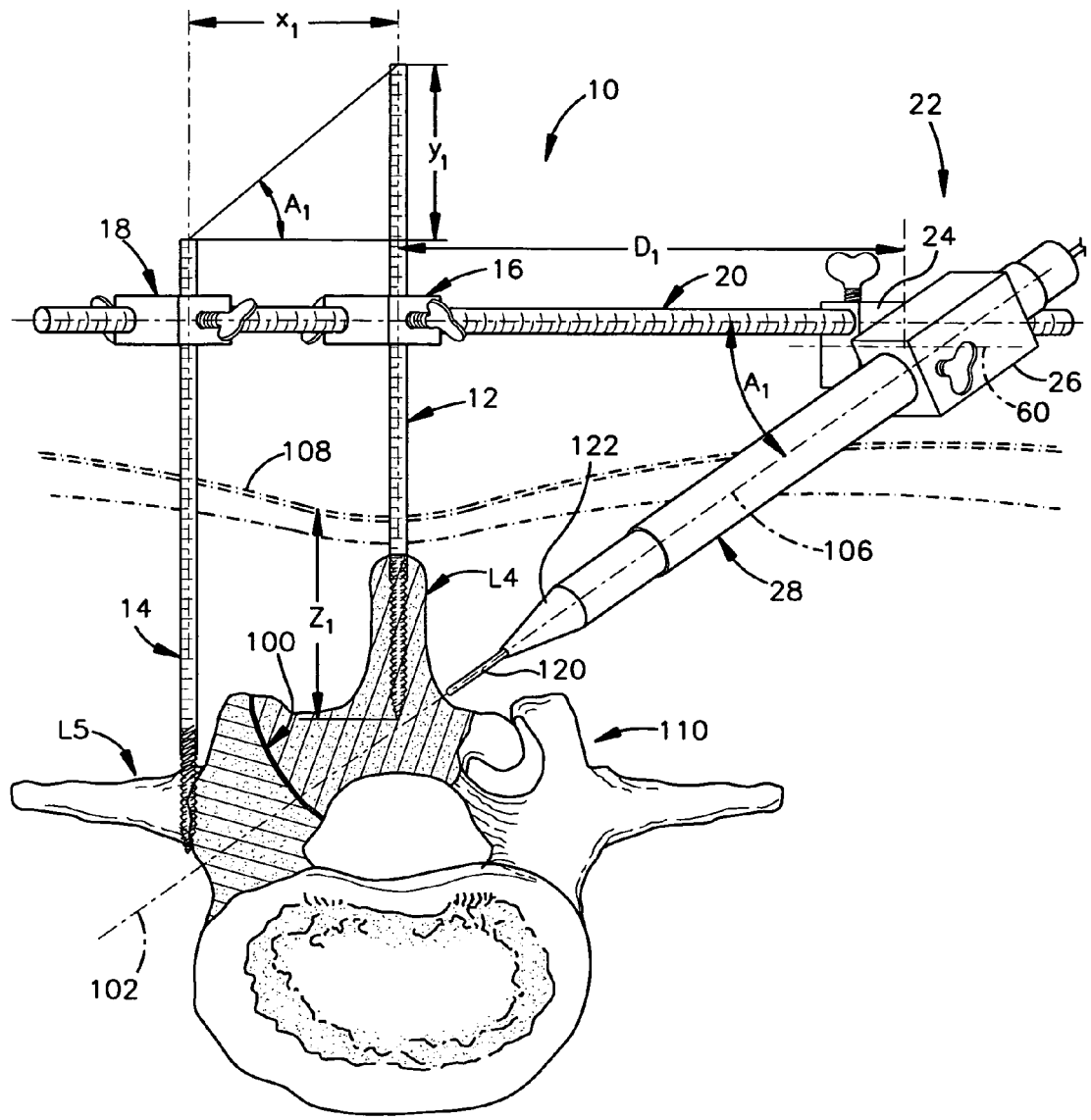

The desired angle $A_1$ for the cannula 28 to extend from the swivel block assembly 22, which provides the trajectory for the implantation of the first screw 200 across the facet joint 100 on the first side 104, is calculated based on the measured X and Y values and the angle between these distances using the following equation: $A_1 = \tan^{-1}(Y_1/X_1)$. As shown in FIG. 13, the calculated angle $A_1$ between the proximal ends 42 of the K-wires 12 and 14 also defines the angle $(A_1)$ between the centerline of the rod member 20 and the centerline 106 of the second passage 64 through the second block member 26. The centerline 106 of the passage 64 is also the centerline of the cannula 28 and is co-linear with the screw trajectory axis 102, as may be seen in FIG. 13. The second block member 26 is then rotated about the axis 60 relative to the first block member 24 to set the desired angle $A_1$ for the centerline 106 of the cannula 28, which extends from the second block member. At the desired angle $A_1$, the first and second rings of serrations 70 and 72 on the first and second block members 24 and 26, respectively, are brought into engagement and secured by the thumbscrew 74 to ensure that the relative angular position of the block members is fixed. It should be understood by those skilled in the art that other means, such as an angle measuring device, for determining the desired angle $A_1$ could also be used in conjunction with the distances $X_1$ and $Y_1$ between the K-wires 12 and 14.

The axial position, or distance, $D_1$ for the swivel block assembly 22 on the rod member 20 is calculated by first measuring the distance $Z_1$ of penetration of the first K-wire 12 (i.e., the distance $Z_1$ extends between the distal tip of the first K-wire and the skin 108) using the graduations on the first K-wire. The distance $D_1$ is then calculated with the following equation: $D_1 = (X_1/Y_1) Z_1$. The distance $D_1$ for the swivel block assembly 22 along the rod member 20 is measured from the centerline of the first K-wire 12 to the axis 60 of the swivel block assembly. The graduations on the rod member 20 or another suitable means can be used for setting the swivel block assembly 22 at the desired axial position. With the swivel block assembly 22 positioned on the rod member 20 and projecting out over the second side 110 (or right side as viewed in FIG. 13) of the L4 and L5 vertebrae, the thumbscrew 54 on the first block member 24 is used to secure the swivel block assembly 22 at the calculated desired axial position $D_1$ on the rod member 20.

The rod member 20 and the swivel block assembly 22 are then lowered to a height above the skin 108 that provides sufficient clearance for the swivel block assembly as shown in FIG. 13. Finally, the first and second fixation blocks 16 and 18 are secured to the first and the second K-wires 12 and 14, respectively, with the thumbscrews 54. The apparatus 10 is now in position for the first screw 200 to be placed across the facet joint 100 on the first side 104 of the L4 and L5 vertebrae.

A scalpel (not shown) may then be used to incise the skin 108 on the second side 110 of the vertebrae to accept the cannula 28. With the cannula 28 temporarily removed, the incision is made using the passage 64 through the second block member 24 of the swivel block assembly 22 to orient the incision along the proper axes 102 and 106. It should be noted that, instead of making another incision on the second side 110 of the vertebrae, it may be possible to utilize the incision previously made for placing bone graft material 160 into the facet joint 142.

Next, under fluoroscopic guidance, a guidewire 120 is passed through the incision along the axes 102 and 106 to the starting point for the screw 200 which is located adjacent the junction of the spinous process and the lamina as shown in FIG. 13. It is contemplated that a Jamshidi needle or other suitable instrument could be used in place of the guidewire 120.

Figure 14:
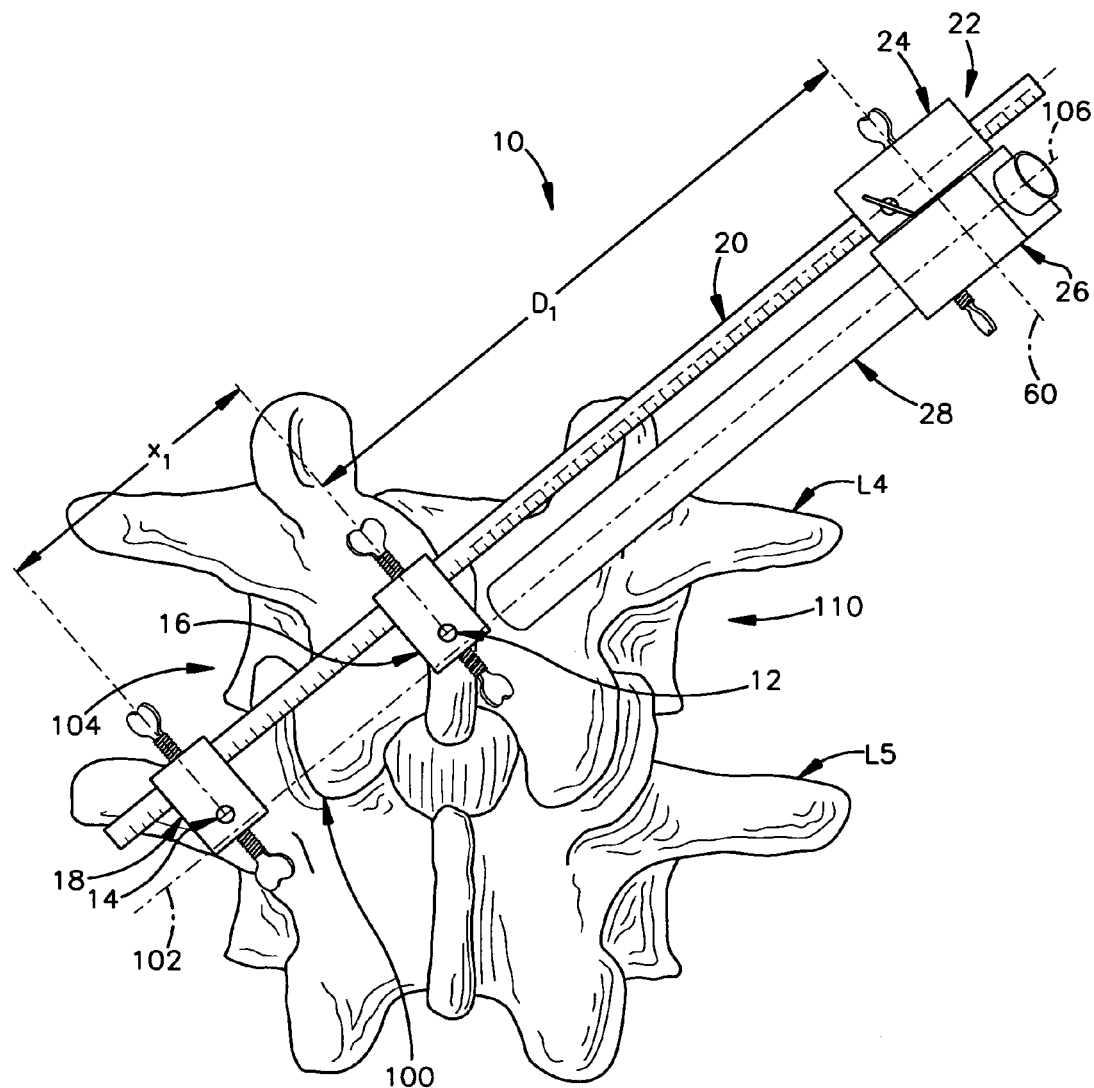
FIG. 14 is a schematic posterior view of the apparatus of FIG. 13.

Next, a blunt obturator 122 is passed over the guidewire 120 to create subcutaneous space for the cannula 28 along the axis 102. The cannula 28, which is guided for movement along the axes 102 and 106 by virtue of the passage 64 through the second block member 26, is then passed over the obturator 122 and the guidewire 120. The cannula 28 is moved along the axes 102 and 106 until the distal end of the cannula docks against the lamina on the second side 110 of the L4 vertebrae as shown in FIGS. 14 and 15. The guidewire 120 and the obturator 122 are then removed from the cannula 28. At this point in the procedure, a small (e.g., 2 mm) diameter scope may be passed down the cannula 28 to inspect the anatomy and the condition of the vertebrae.

After ensuring that all of the thumbscrews 54 and 74 are secure and that the alignment of the axis 102 is correct, a drill bit (not shown) may be inserted into the cannula 28 to drill a pilot hole along the axis 102 through the lamina on the second side 110 of the L4 vertebrae, through the inferior articular process on the first side 104 of the L4 vertebrae, across the facet joint 100 on the first side, and into the superior articular process of the L5 vertebrae. It is contemplated that a drill guide (not shown) could be used to center the drill bit in the cannula 28 and ensure that the pilot hole extends along the axis 102. It should be understood, however, that a pilot hole need not be drilled, especially if the screw 200' illustrated in FIG. 6A (with the drill tip 212) is to be used.

Figure 16:
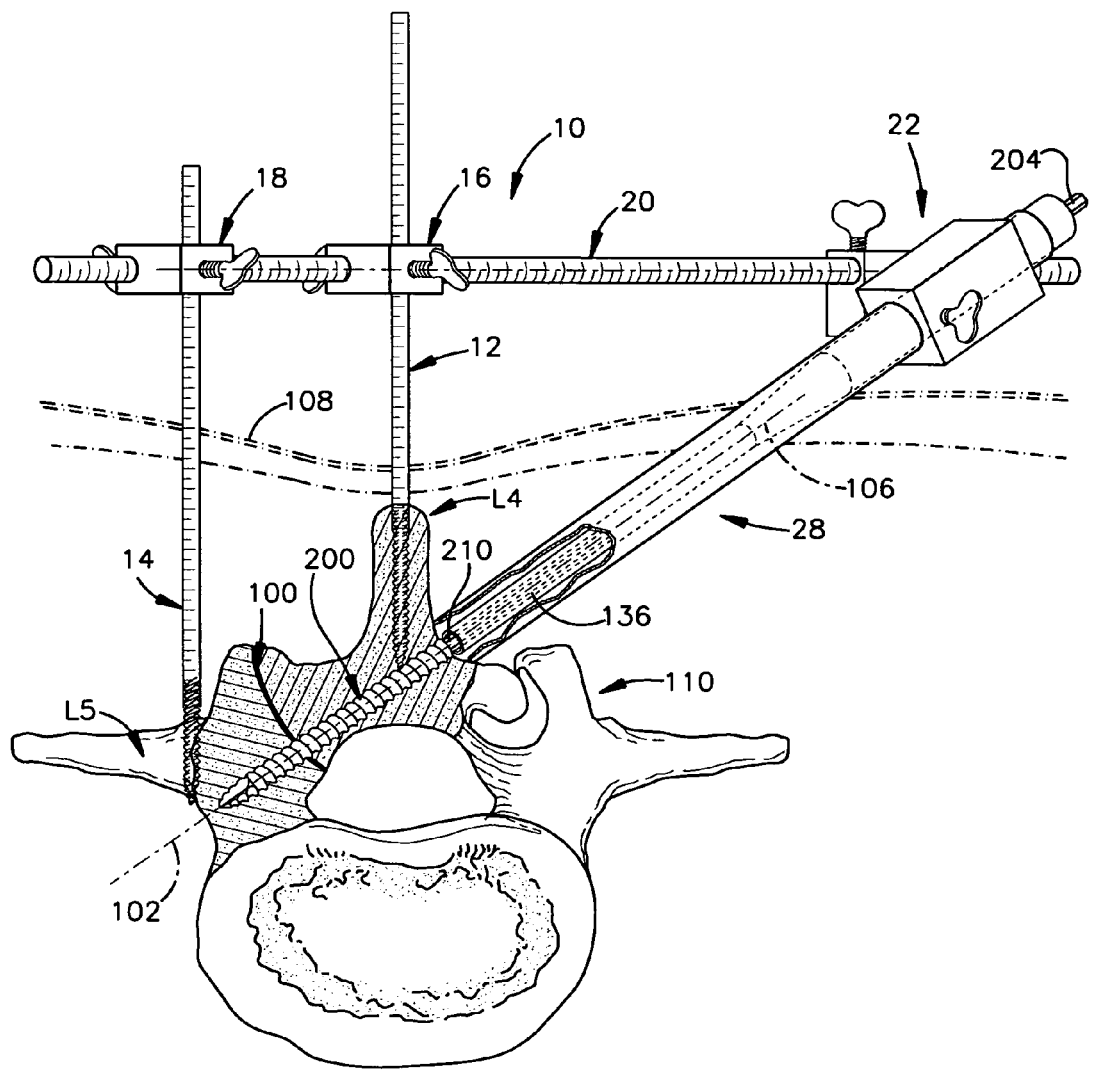
FIG. 16 is a view similar to FIG. 13 illustrating the implantation of a facet screw according to the inventive method.
Figure 17:
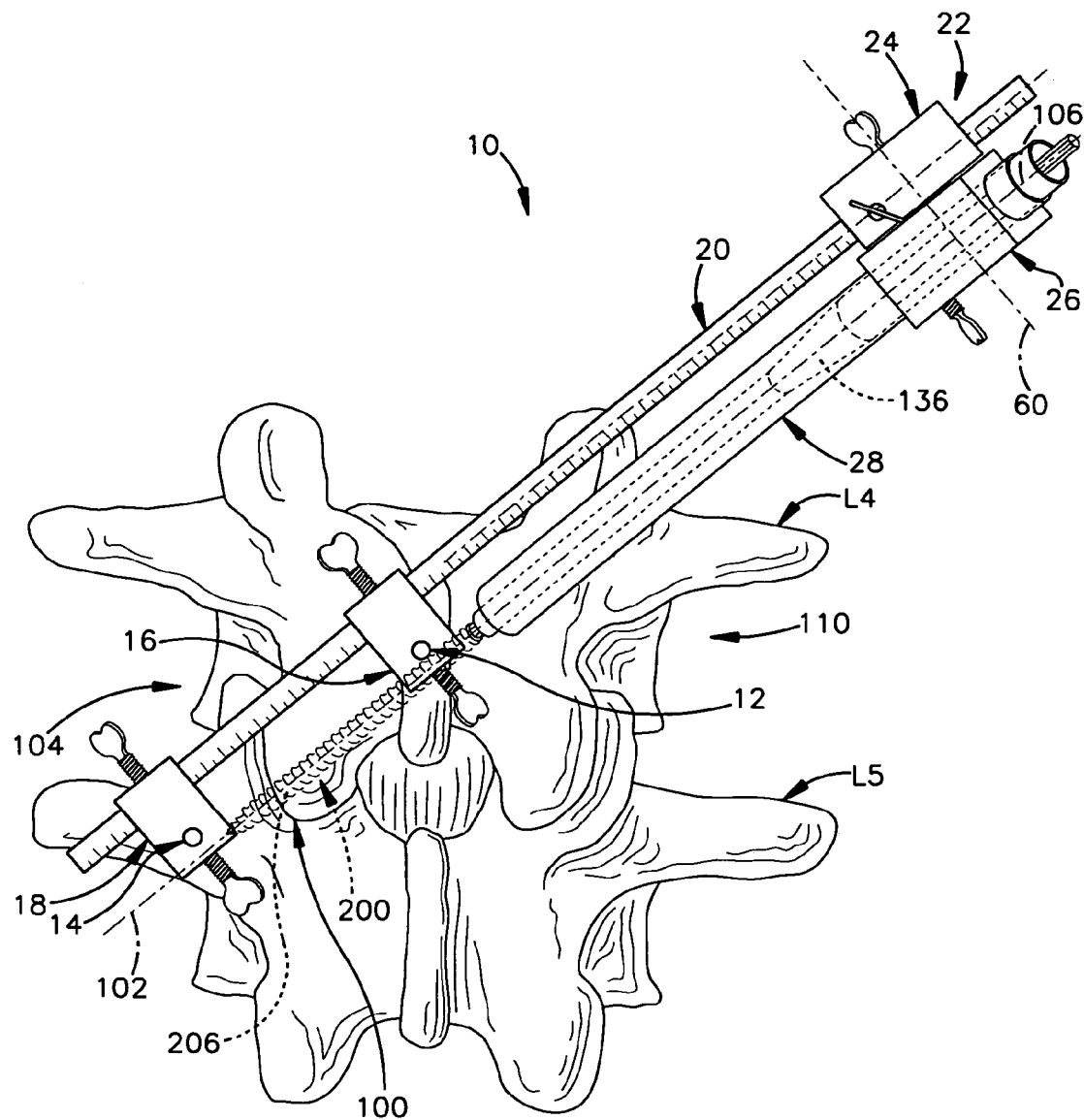
FIG. 17 is a posterior view of the apparatus of FIG. 16.
Figure 18:
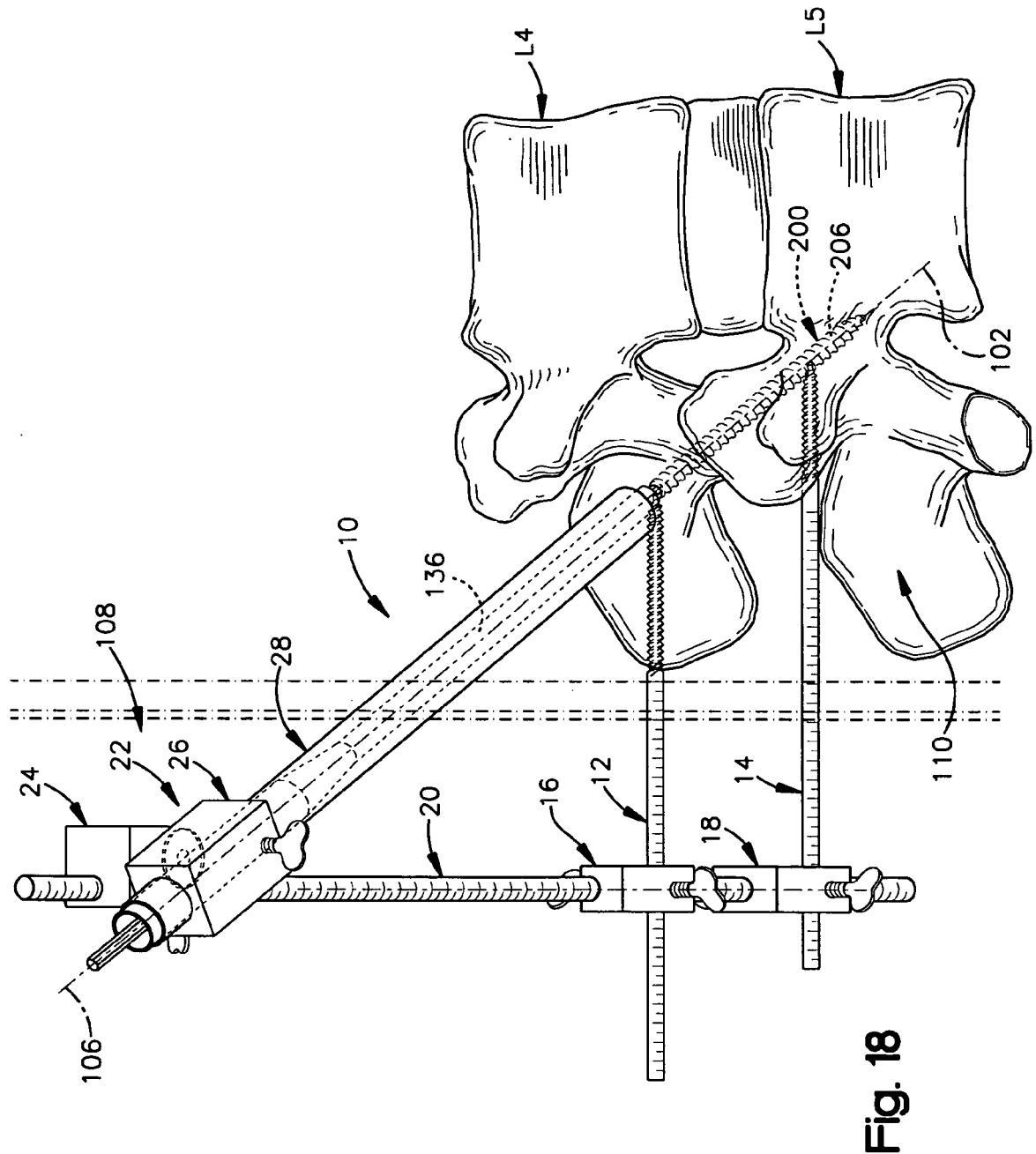
FIG. 18 is a side view of the apparatus of FIG. 17.
Figure 33:
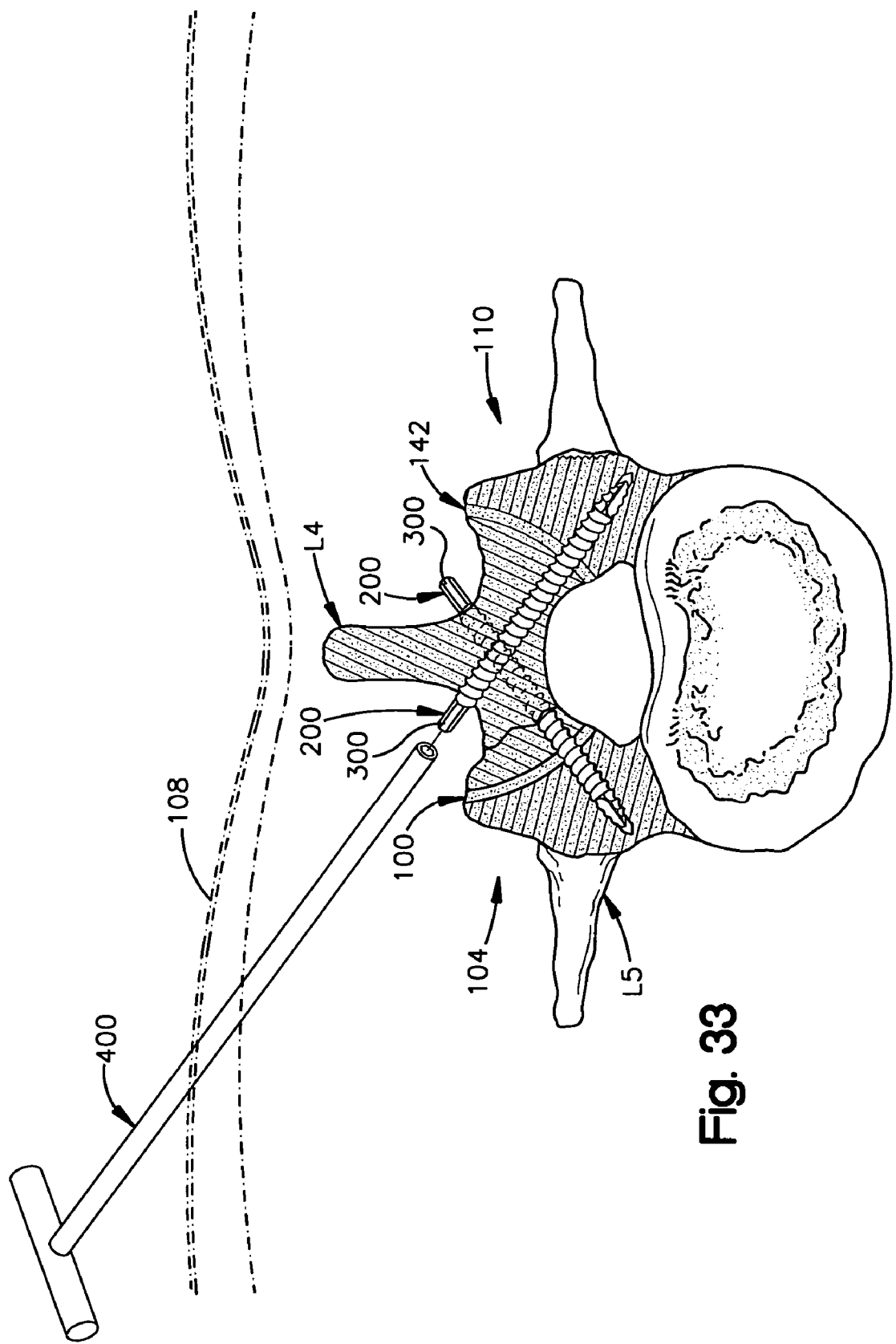
FIG. 33 is a view similar to FIG. 32 illustrating removal of one of the screws in accordance with the present invention.

As shown in FIG. 16, the self-tapping screw 200 is then inserted into the cannula 28 and screwed into the L4 and L5 vertebrae along the axis 102 using a driver 400 (FIG. 33). In the illustrated embodiment, the threaded section 206 of the screw 200 has a major diameter that is slightly less than the inner diameter of a second cannula 136 that is inserted into the cannula 28 to aid in keeping the screw aligned on the axis 102 during implantation. Further, the illustrated driver 400 has a hexagonal socket for receiving the hexagonal outer surface of the screw 200, although it should be understood that the outer surface of the screw and the corresponding driver socket could utilize a different geometry. The screw 200 is advanced until all of the threaded section 206 is received within the L4 and L5 vertebrae as shown in FIGS. 16-18. Fluoroscopic guidance coupled with the aforementioned calculation to select the length $L_1$ of the threaded section 206 of the screw 200 ensures that the distal tip of the screw does not penetrate beyond the cortex of the L5 vertebrae. As implanted, the threaded section 206 of the screw 200 extends across the facet joint 100 to connect the inferior articular process of the L4 vertebrae to the superior articular process of the L5 vertebrae.

Figure 19:
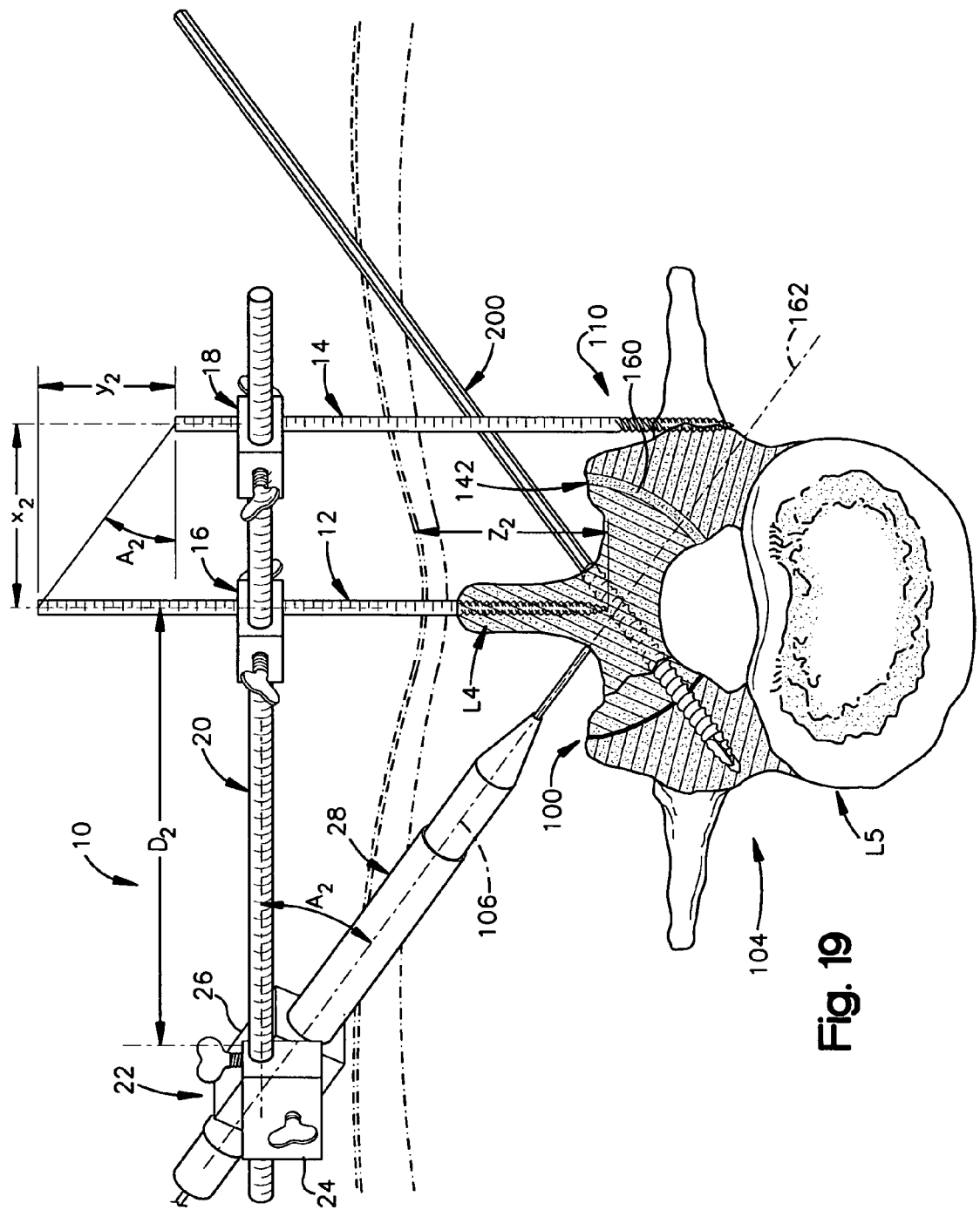
FIG. 19 is a view similar to FIG. 16 illustrating components of the apparatus of FIG. 1 in different positions for placing a facet screw across a facet joint on the opposite side.
Figure 20:
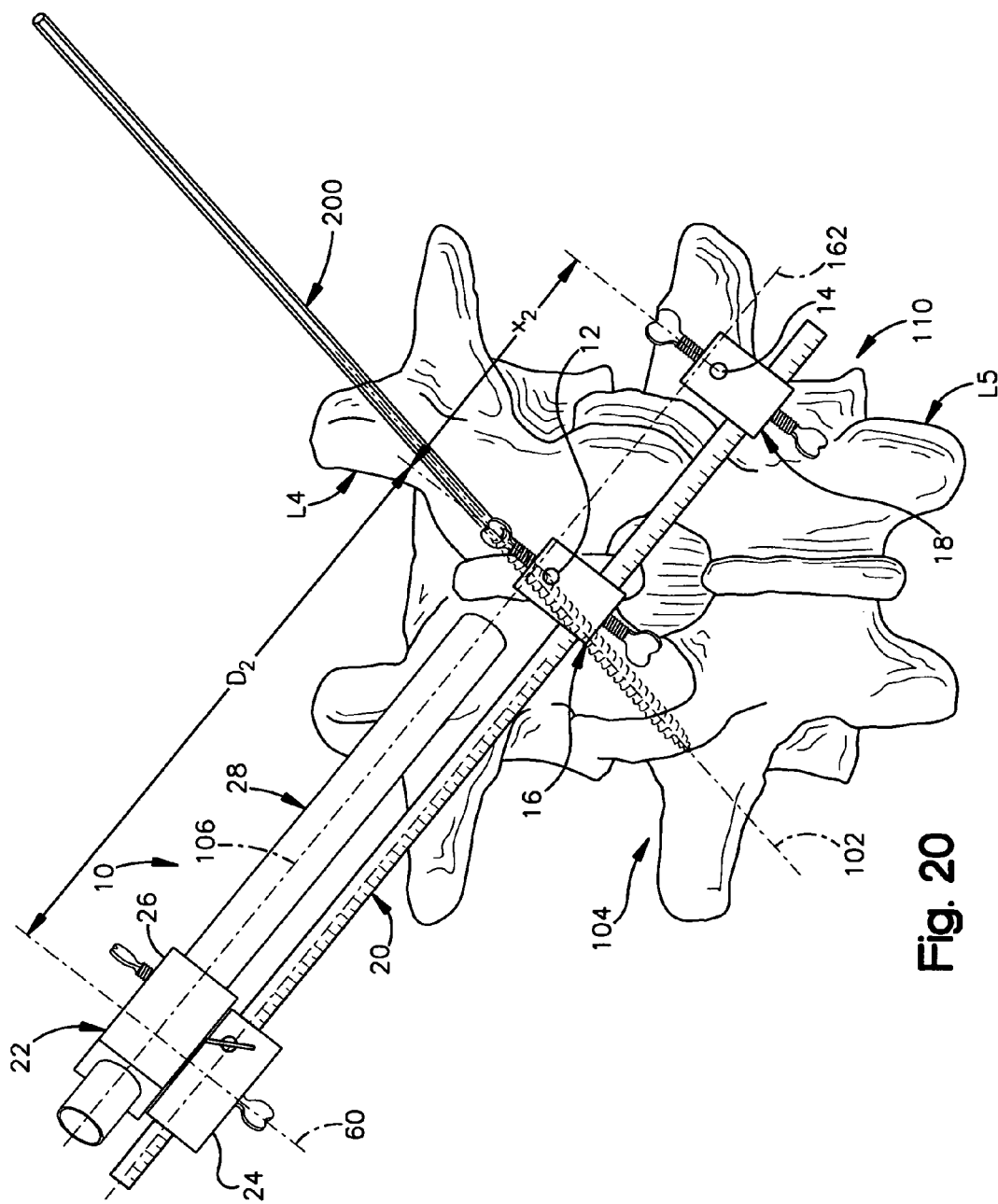
FIG. 20 is a schematic posterior view of the apparatus at a subsequent stage to that of FIG. 19.
Figure 21:
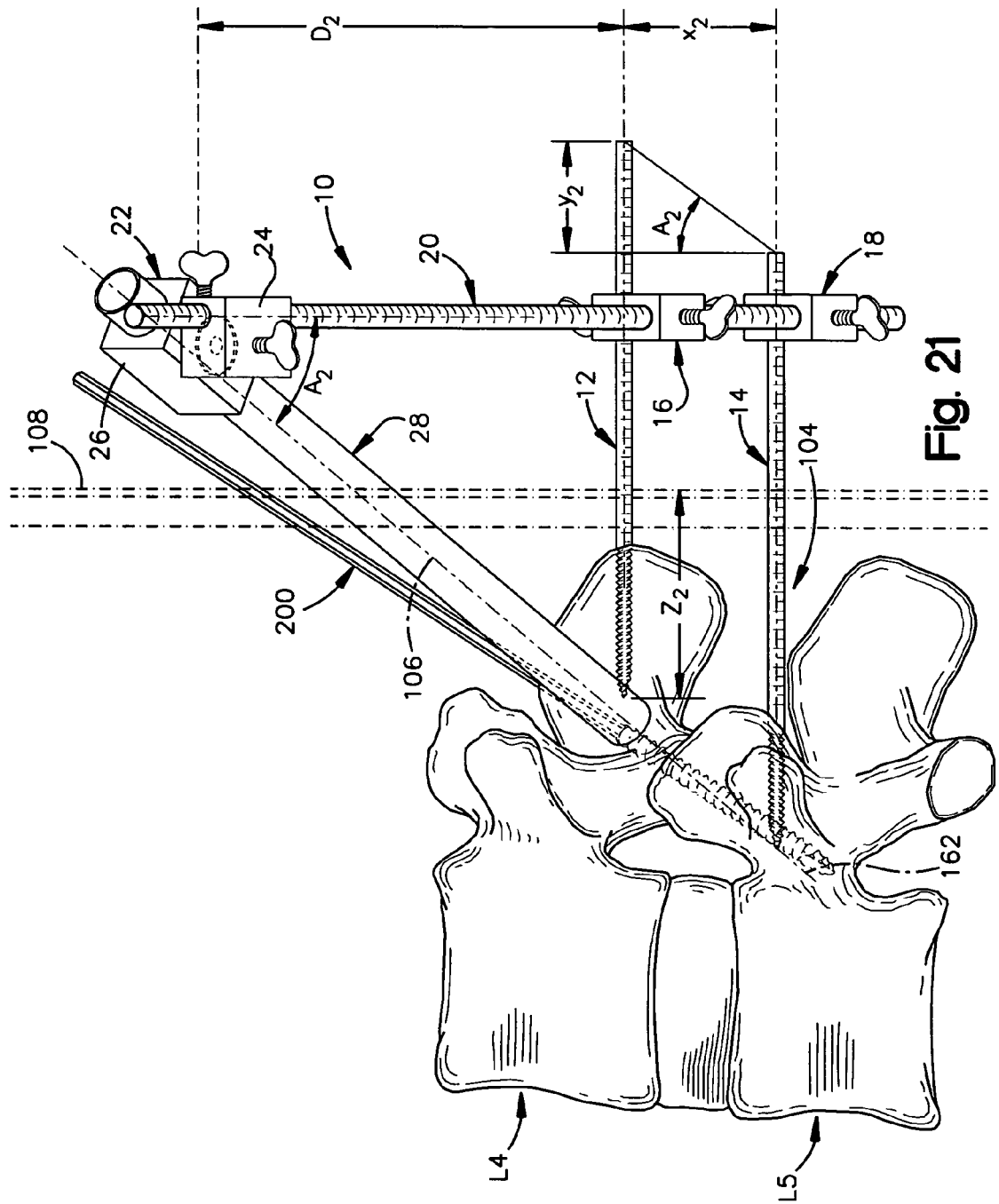
FIG. 21 is a schematic side view of the opposite side shown in FIG. 19.

The next steps in the process are to loosen all of the thumbscrews 54 and 74, remove the fixation blocks 16 and 18 from the K-wires 12 and 14, and disassemble the swivel block assembly 22 from the rod member 20. The second K-wire 14 is then removed from the transverse process on the first side 104 of the L5 vertebrae. Next, through another percutaneous stab incision, the second K-wire 14 is inserted into the transverse process on the second side 110 of the L5 vertebrae so that it again extends in parallel with the first K-wire 12 in both the sagittal and coronal planes as shown in FIGS. 19-21. The distal end 40 of the second K-wire 14 is screwed into the transverse process just lateral to the facet joint 142 on the second side 110 of the vertebrae up to the junction of the transverse process and the pedicle.

The first fixation block 16 is then slid onto the first K-wire 12 with the first K-wire extending into the first passage 50 in the first fixation block. Similarly, the second fixation block 18 is slid onto the second K-wire 14 with the second K-wire extending into the first passage 56 in the second fixation block. The first end 30 of the rod member 20 is slid then into the second passages 52 and 58 in the first and second fixation blocks 16 and 18, respectively, so that it extends across the first and second K-wires 12 and 14. The thumbscrews 54 that extend into the second passages 52 and 58 are tightened to secure the rod member 20 to the fixation blocks 16 and 18.

Once again, the next steps in the process involve calculations to determine the following three parameters: (1) the length $L_2$ of the threaded section 206 of a second screw 200 to be implanted; (2) the desired angle $A_2$ for the cannula 28 to extend from the swivel block assembly, which provides a trajectory axis 162 for the implantation of the second screw 200 across the facet joint 142 on the second side 110; and (3) the desired axial position $D_2$ for the swivel block assembly 22 along the rod member 20. As mentioned above, the apparatus 10 according to the present invention utilizes the position and relationship of the first and second K-wires 12 and 14 to determine the entry point and trajectory upon which the second screw 200 is implanted into the L4 and L5 vertebrae.

The length $L_2$ of the threaded section 206 is determined by measuring the axial difference $X_2$ between the two identical K-wires 12 and 14 and measuring the horizontal difference $Y_2$ between the two K-wires. The graduations on the K-wires 12 and 14 or another suitable means can assist in taking these measurements. The length $L_2$ is then calculated with the following equation: $L_2=\sqrt{(X_2^2+Y_2^2)}$. Use of this equation to determine the desired screw length $L_2$ helps to ensure that the second screw 200, when implanted across the facet joint 142, will not extend beyond the cortex of the superior articular process where nerve damage could become an issue. It should be noted that in many cases, the lengths for the threaded sections 206 of the first and second screws 200 will likely be the same.

The desired angle $A_2$ for the cannula 28 to extend from the swivel block assembly 22, which provides the trajectory for the implantation of the second screw 200 across the facet joint 142 on the second side 110, is calculated with the following equation: $A_2=\tan^{-1}(Y_2/X_2)$. As shown in FIG. 19, the calculated desired angle $A_2$ between the proximal ends 42 of the K-wires 12 and 14 also defines the angle ($A_2$) between the centerline of the rod member 20 and the centerline 106 of the second passage 64 through the second block member 26. The centerline of the passage 64 is also the centerline of the cannula 162, as may be seen in FIG. 19. The second block member 26 is then rotated about the axis 60 relative to the first block member 24 to set the desired angle $A_2$ for the centerline 106 of the cannula 28, which extends from the second block member. At the desired angle $A_2$, the first and second rings of serrations 70 and 72 on the first and second block members 24 and 26, respectively are brought into engagement and secured by the thumbscrew 74 to ensure that the relative angular position of the block members is fixed. It should be understood by those skilled in the art that other means, such as an angle measuring device, for determining the desired angle $A_2$ could also be used in conjunction with the distances $X_2$ and $Y_2$ between the K-wires 12 and 14.

The axial position, or distance, $D_2$ for the swivel block assembly 22 on the rod member 20 is calculated by first measuring the distance $Z_2$ of penetration of the first K-wire 12 (i.e., the distance $Z_2$ extends between the distal tip of the first K-wire and the skin 108) using the graduations on the first K-wire. The distance $D_2$ is then calculated with the following equation: $D_2=(X_2/Y_2)Z_2$. The distance $D_2$ for the swivel block assembly 22 along the rod member 20 is measured from the centerline of the first K-wire 12 to the axis 60 of the swivel block assembly 22. The graduations on the rod member 20 or another suitable means can be used for setting the swivel block assembly 22 at the desired axial position.

Next, the swivel block assembly 22 is then slid onto the second end 32 of the rod member 20, which is projecting out over the first side 104 of the vertebrae, with the rod member extending through the passage 62 in the first block member 24. The thumbscrew 54 is used to secure the swivel block assembly 22 at the calculated desired axial position $D_2$ on the rod member 20.

The rod member 20 and the swivel block assembly 22 are then lowered to a height above the skin 108 that provides sufficient clearance for the swivel block assembly as shown in FIG. 19. Finally, the first and second fixation blocks 16 and 18 are secured to the first and second K-wires 12 and 14, respectively, with the thumbscrews. The apparatus 10 is now in position for the second screw 200 to be placed across the facet joint 142 on the second side 110 of the vertebrae. It is important to note at this point that the predetermined offset between the first and second passages 50 and 52 in the first fixation blocks 16 and the first and second passages 56 and 58 in the second fixation block 18 positions the rod member 20 and the swivel block assembly 22 so that the axis 162 for implantation of the second screw 200 is offset from the axis 102 on which the first screw 200 was implanted. This offset ensures that the second screw 200 does not intersect with the first screw 200 as it extends through the spinous process of the L4 vertebrae.

The scalpel (not shown) is used to incise the skin 108 on the first side 104 of the vertebrae to accept the cannula 28. With the cannula 28 temporarily removed, the incision is made using the passage 64 through the second block member 24 of the swivel block assembly 22 to orient the incision on the axes 106 and 162. Under fluoroscopic guidance, the guidewire 120 is passed through the incision along the axes 106 and 162 to the starting point for the second screw 200 which is located adjacent the junction of the spinous process and the lamina as shown in FIG. 19. As discussed above, it is contemplated that a Jamshidi needle or other suitable instrument could be used in place of the guidewire 120.

Next, the blunt obturator 122 is passed over the guidewire 120 to create subcutaneous space for the cannula 28 along the axis 162. The cannula 28, which is guided for movement along the axes 106 and 162 by virtue of the passage 64 through the second block member 26, is then passed over the obturator 122 and the guidewire 120. The cannula 28 is moved along the axes 106 and 162 until the distal end of the cannula docks against the lamina on the first side 104 of the L4 vertebrae as shown in FIGS. 20 and 21. The guidewire 120 and the obturator 122 are then removed from the cannula 28. At this point in the procedure, the small diameter scope may again be passed down the cannula 28 to inspect the anatomy and the condition of the vertebrae.

After ensuring that all of the thumbscrews 54 and 74 are secure and that the alignment of the axis 162 is correct, a drill bit (not shown) may be inserted into the cannula 28 to drill a pilot hole along the axis 162 through the lamina on the first side 104 of the L4 vertebrae, through the inferior articular process on the second side 110 of the L4 vertebrae, across the facet joint 142 and the bone graft material 160 therein, and into the superior articular process of the L5 vertebrae. It is contemplated that a drill guide (not shown) could be used to center the drill bit in the cannula 28 and ensure that the pilot hole extends along the axis 102. It should be understood, however, that a pilot hole need not be drilled, especially if the screw 200' illustrated in FIG. 6A (with the drill tip 212) is to be used.

Figure 22:
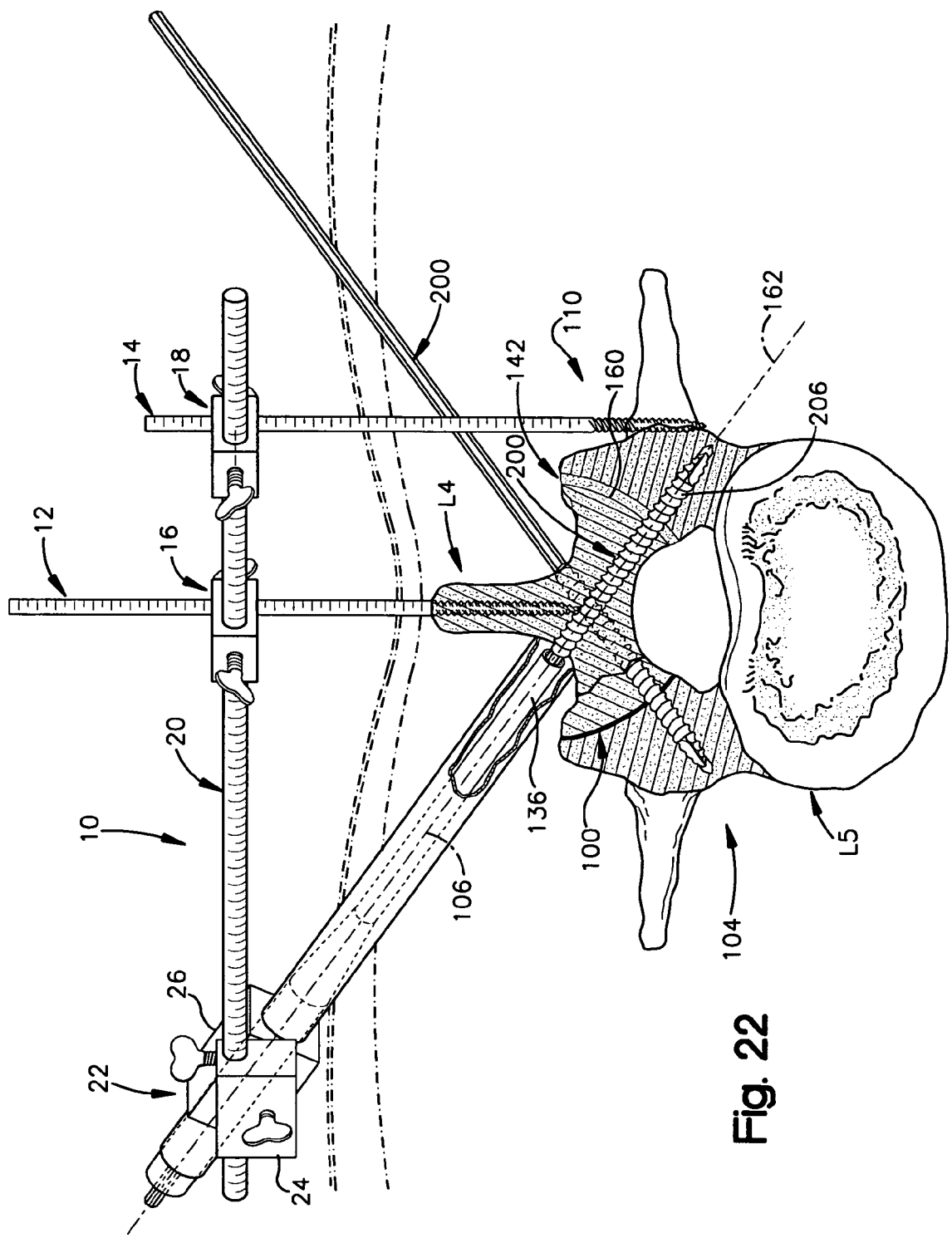
FIG. 22 is a view similar to FIG. 19 illustrating the implantation of a second facet screw according to the inventive method.
Figure 23:
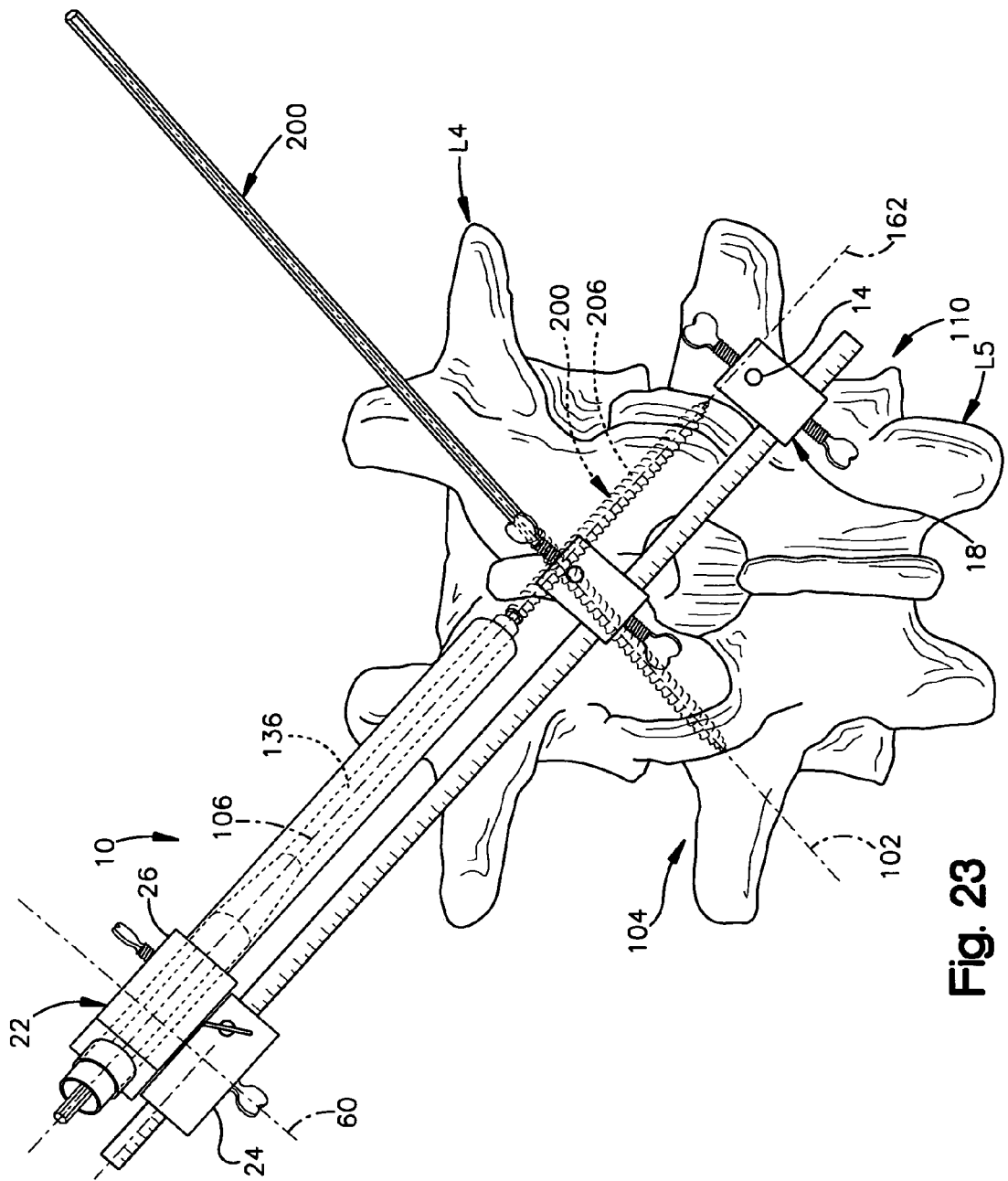
FIG. 23 is a posterior view of the apparatus of FIG. 22.
Figure 24:
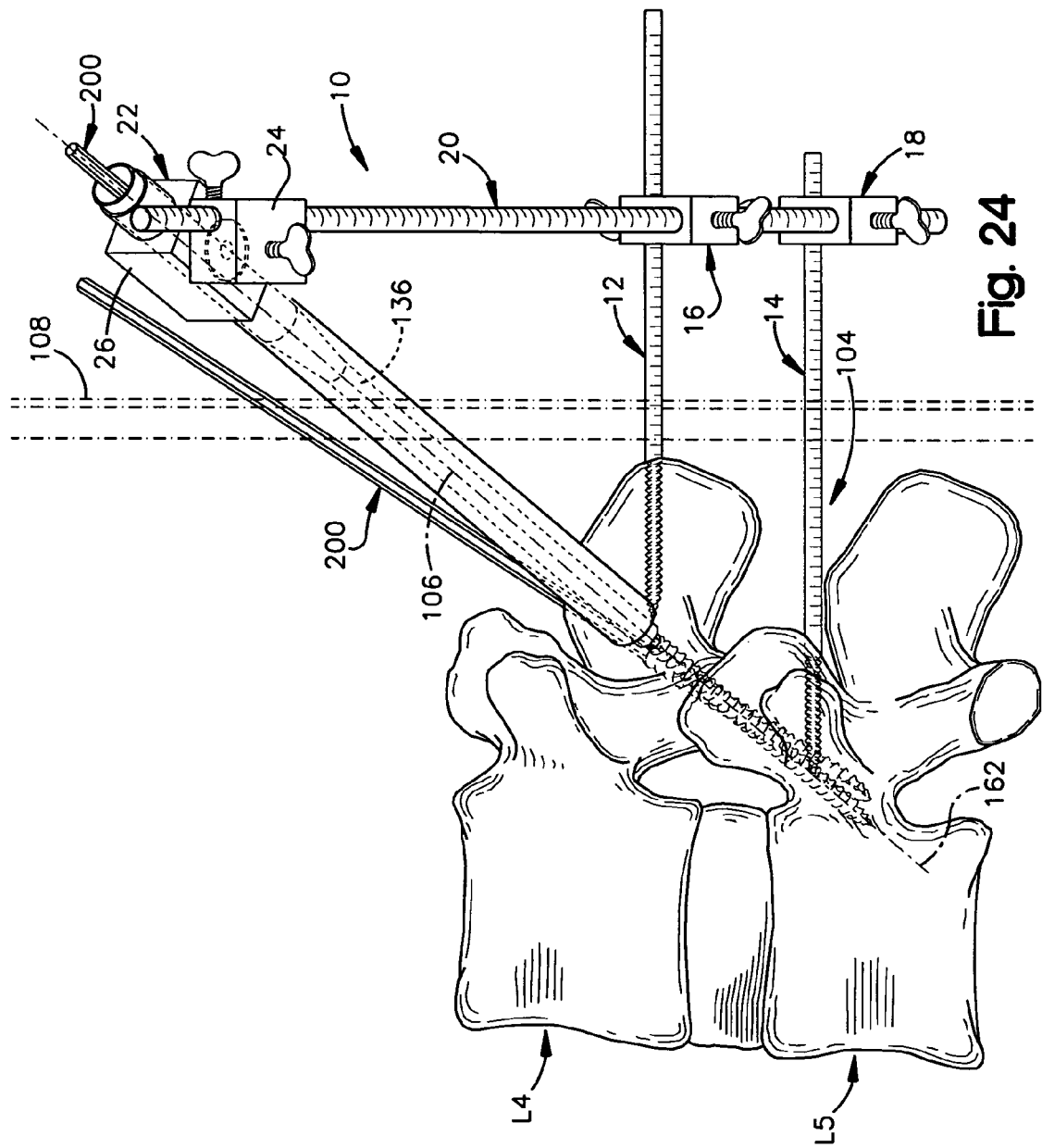
FIG. 24 is a side view of the apparatus of FIG. 23.

As shown in FIG. 22, the self-tapping screw 200 is then inserted into the cannula 28 and screwed into the L4 and L5 vertebrae along the axis 162 using the driver 400 (FIG. 33). In the illustrated embodiment, the threaded section 206 of the screw 200 has a major diameter that is slightly less than the inner diameter of the second cannula 136 that is inserted into the cannula 28 to aid in keeping the screw aligned on the axis 162 during implantation. Further, the illustrated driver 400 has a hexagonal socket for receiving the hexagonal outer surface of the screw 200, although it should be understood that the outer surface of the screw and the corresponding driver socket could utilize a different geometry. The screw 200 is advanced until all of the threaded section 206 is received within the L4 and L5 vertebrae as shown in FIGS. 22-24. Fluoroscopic guidance coupled with the aforementioned calculation to select the length $L_1$ of the threaded section 206 of the screw 200 ensures that the distal tip of the screw does not penetrate beyond the cortex of the L5 vertebrae. As implanted, the threaded section 206 of the screw 200 extends across the facet joint 142 to connect the inferior articular process of the L4 vertebrae to the superior articular process of the L5 vertebrae.

With the second screw 20 implanted, the cannula 28 is removed from the skin 108 and the thumbscrew 74 is released to allow relative movement of the first and second block members 24 and 26. The second block member 26 is then swiveled to aim the centerline 106 of the cannula 28 along an axis 170 (FIG. 25) that extends toward the facet joint 100 on the first side 104 of the vertebrae. In order to aim the cannula 28 toward the facet joint 100, the other thumbscrews 54 may also be released to allow additional movement of the swivel block assembly 22. Releasing the other thumbscrews 54 may allow the cannula to be positioned over the existing incision while being aimed toward the facet joint 100 along the axis 170 so that the same incision can be utilized again.

Figure 25:
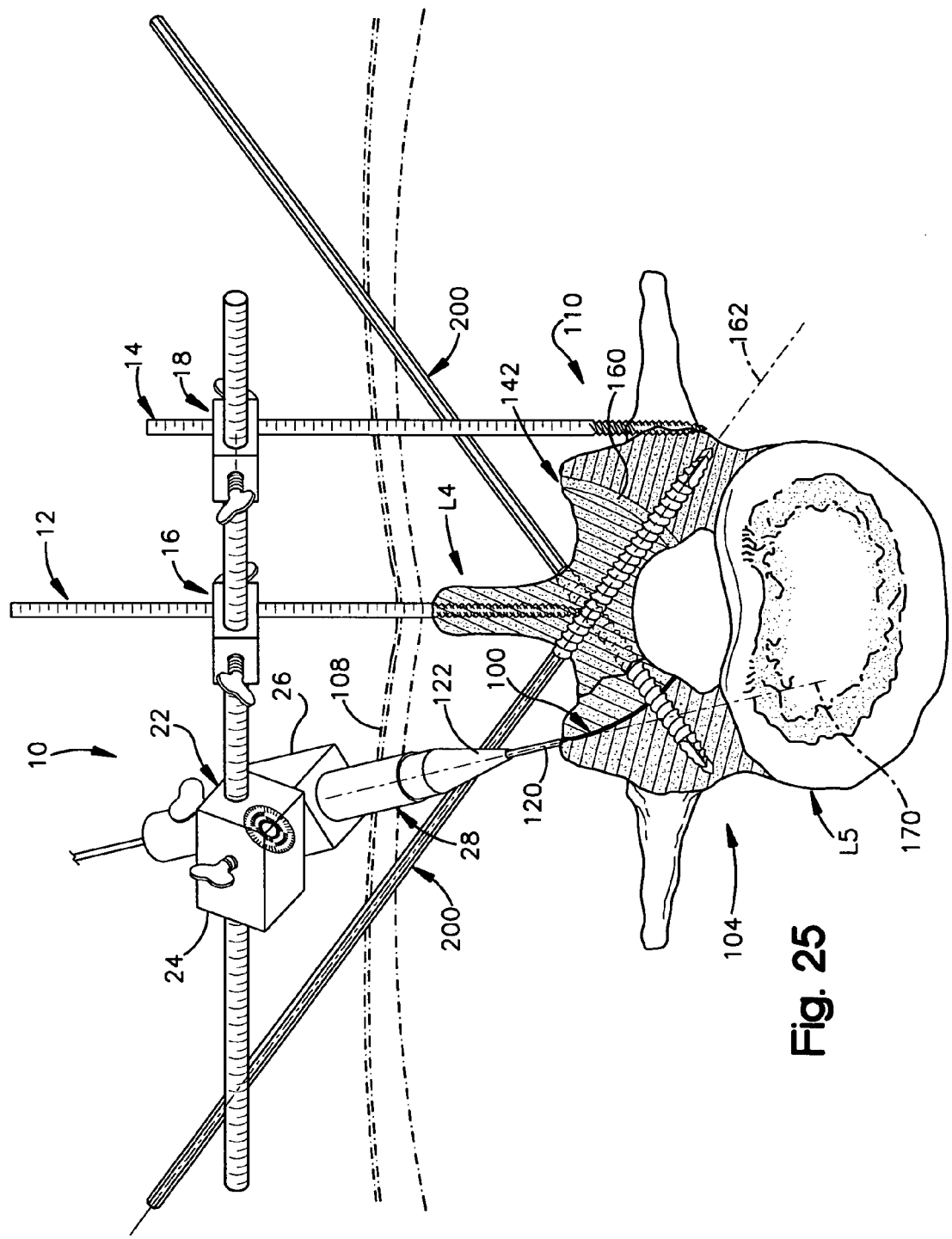
FIG. 25 is a view similar to FIG. 22 illustrating a subsequent step.
Figure 26:
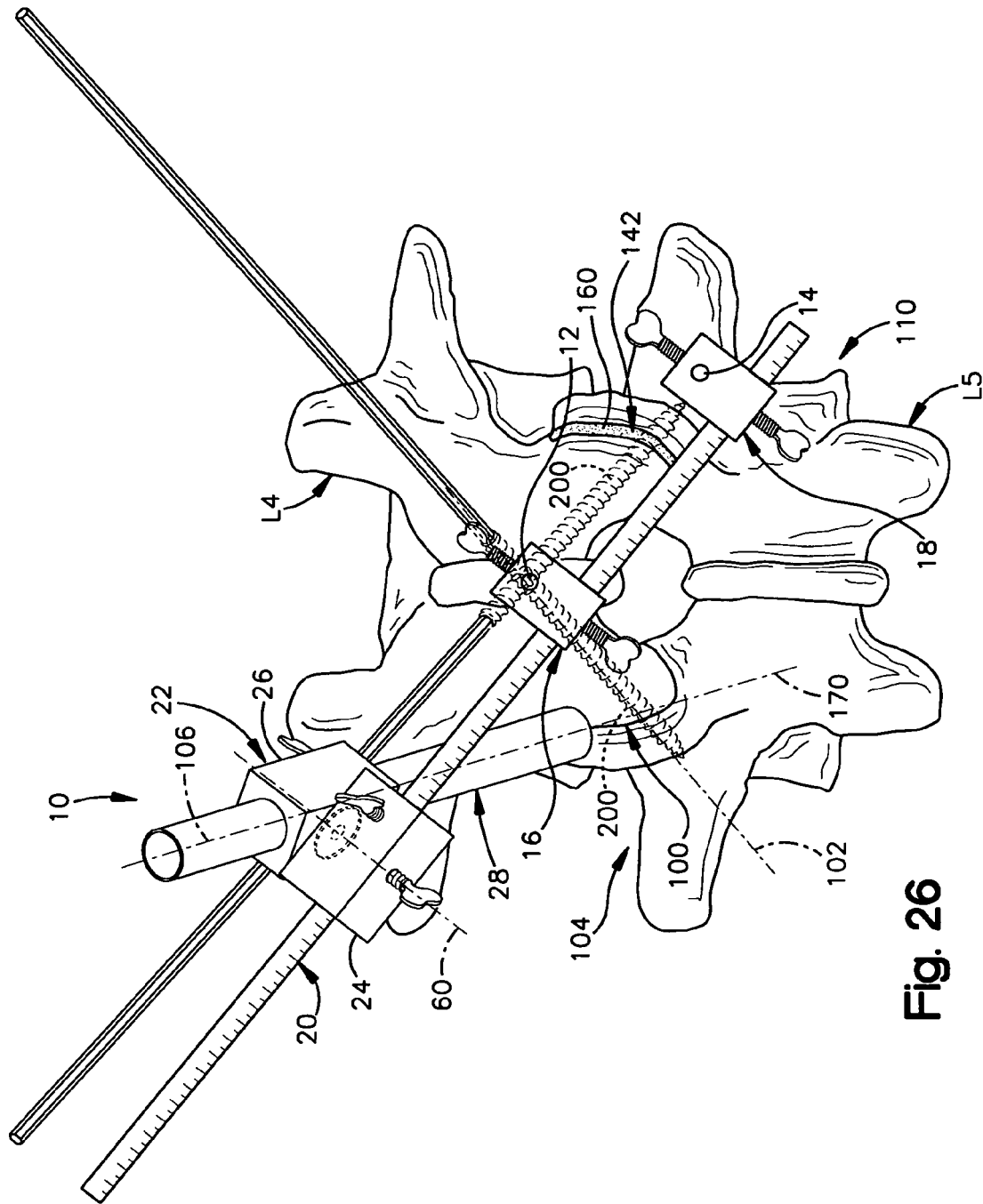
FIG. 26 is a posterior view of the apparatus of FIG. 25 at a subsequent stage.
Figure 27:
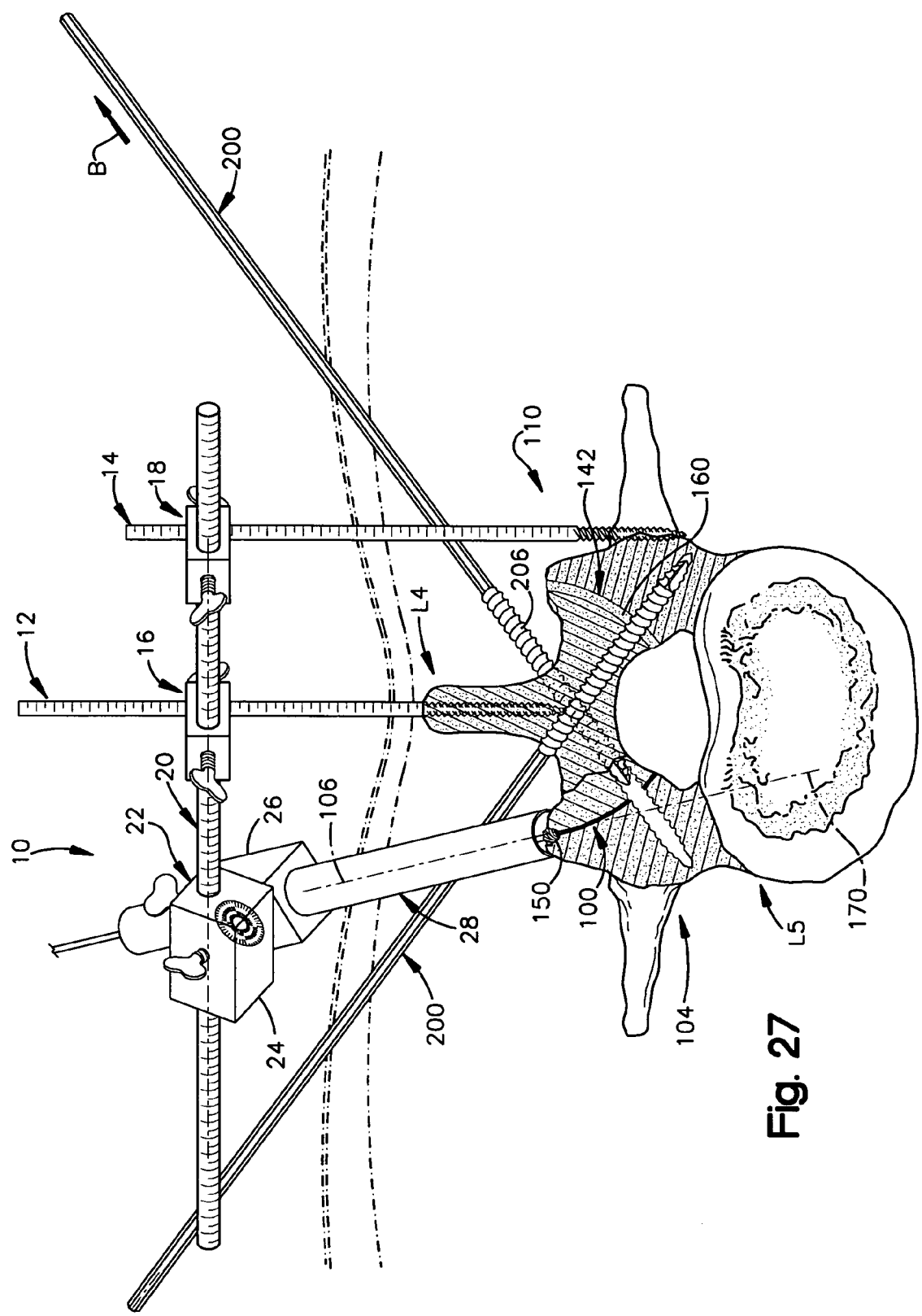
FIGS. 27-32 are views similar to FIG. 25 illustrating the final stages of the method for fusing adjacent vertebrae according to the inventive method.

After tightening all of the thumbscrews 54 and 74 to secure the components of the apparatus 10 in the positions shown in FIG. 25, the guidewire 120 (or Jamshidi needle, etc.) is passed through the incision along the axis 170 to the surface of the facet joint 100 on the first side 104 of the vertebrae under fluoroscopic guidance. Next, the blunt obturator 122 is passed over the guidewire 120 to create subcutaneous space for the cannula 28 along the axis 170. The cannula 28, which is guided for movement along the axes 106 and 170 by virtue of the passage 64 through the second block member 26, is then passed over the obturator 122 and the guidewire 120. The cannula 28 is moved along the axes 106 and 170 until the distal end of the cannula docks against the surface of the facet joint 100 as shown in FIGS. 26 and 27. The guidewire 120 and the obturator 122 are then removed from the cannula 28. As may be seen in FIG. 27, the first screw 200 inserted across the facet joint 100 on the first side 104 of the vertebrae is then backed out of the facet joint as indicated by arrow B.

After ensuring that all of the thumbscrews 54 and 74 are secure and that the alignment of the axis 170 is correct, the burring bit 150 (FIG. 27) is inserted into the cannula 28. The burring bit 150 is rotated by a drill (not shown) to burr the opposing surfaces 172 and 174 of the inferior articular process and the superior articular process on the first side 104 of the L4 and L5 vertebrae, respectively. Burring these surfaces 172 and 174 widens the facet joint 100 so that a bone graft material is more easily placed into the facet joint. It is contemplated that the cannula 28 may be moved slightly along the facet joint 100 during the burring process in order to access a larger area of the facet joint with the burring bit 150. It should be noted that it is not required that the first screw 200 be backed out of the facet joint 100 in order to burr the facet joint. If, however, the first screw 200 is not backed out before burring, care must be taken to burr around, but not contact, the previously implanted first screw.

Figure 28:
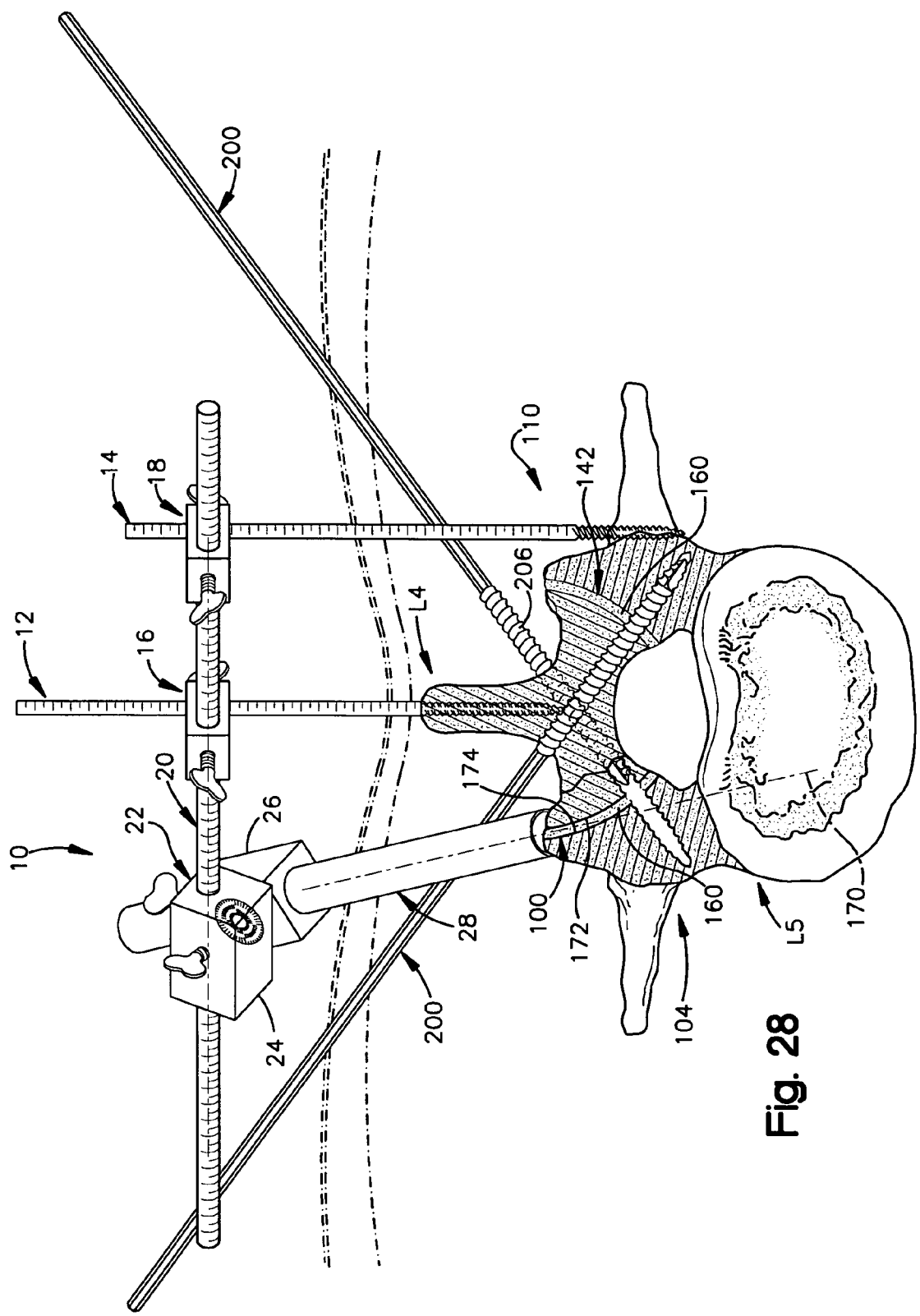
Figure 29:
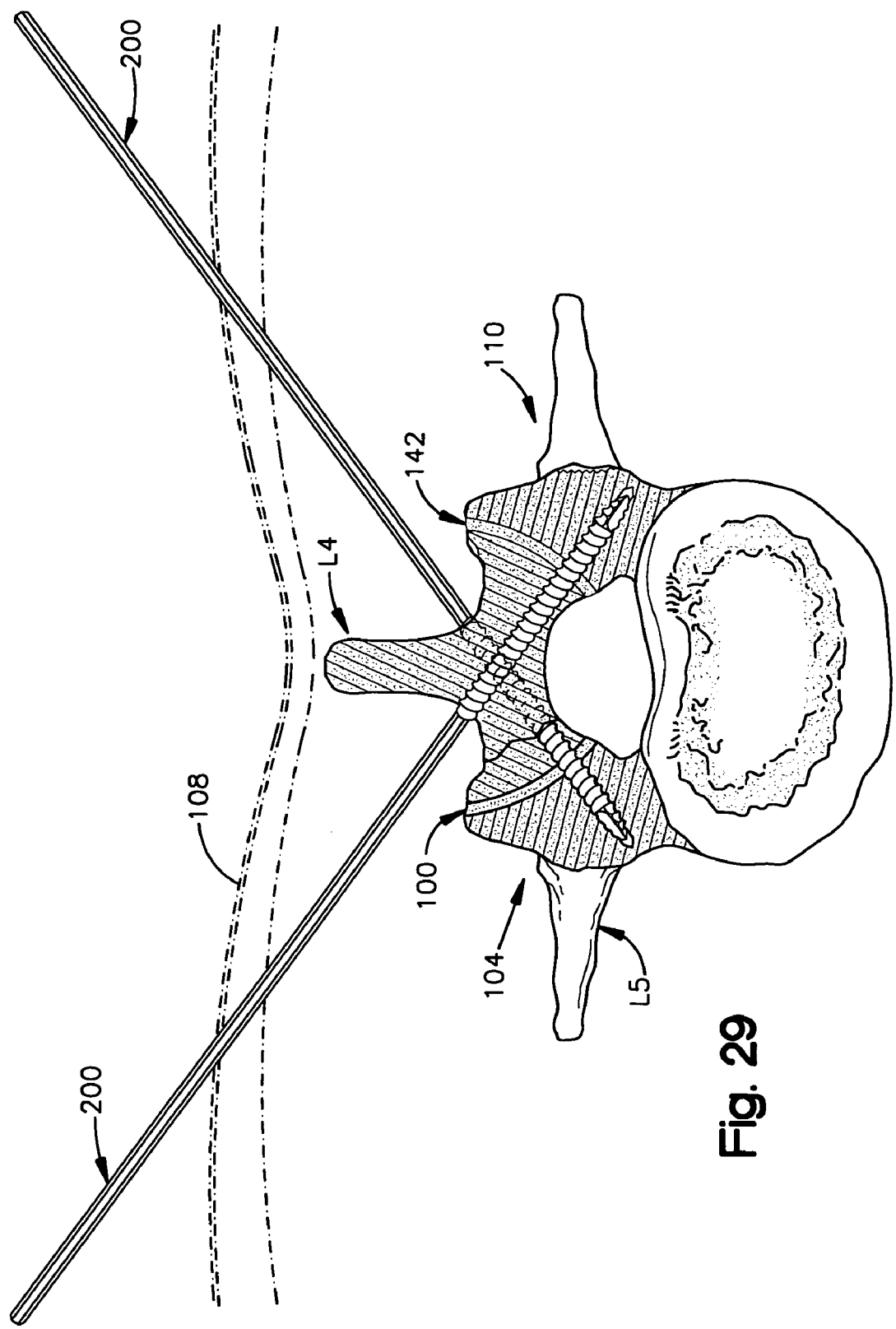

After the articular surfaces 172 and 174 of the facet joint 100 on the first side 104 of the vertebrae have been burred out around the first screw 200, bone graft (or bone substitute) material 160 (FIG. 28) for helping to fuse the L4 and L5 vertebrae is placed into the facet joint 100 through the cannula 28. The bone graft material 160 may be fed into the facet joint using any known suitable instrument(s). As shown in FIG. 29, after the bone graft material 160 has been placed in the facet joint 100, the first screw 200 is returned to its previous position across the facet joint. The cannula 28 is then removed from the incision on the first side 104 of the vertebrae and the first and second K-wires 12 and 14 are removed from the L4 and L5 vertebrae, respectively.

Figure 30:
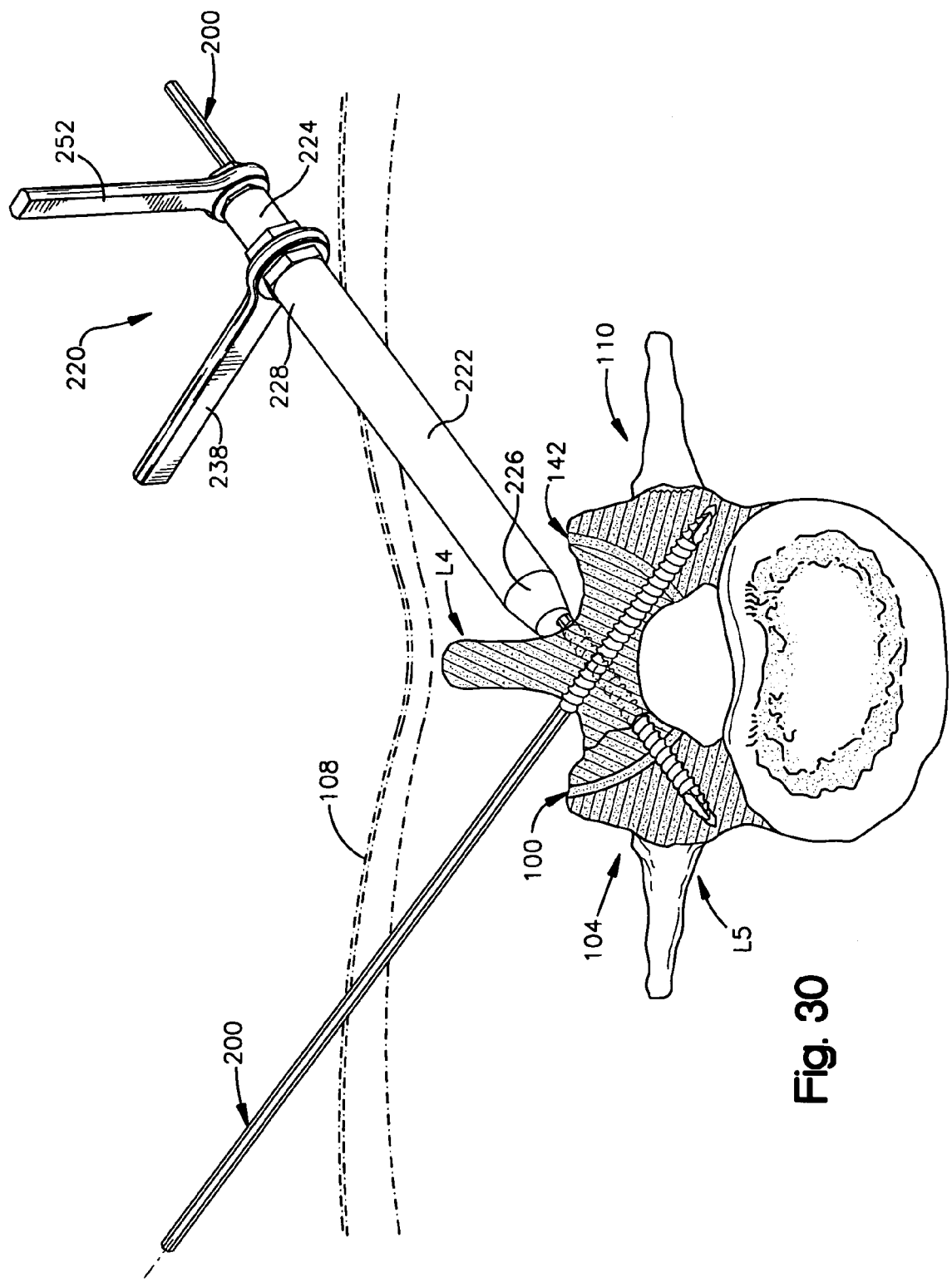
Figure 31:
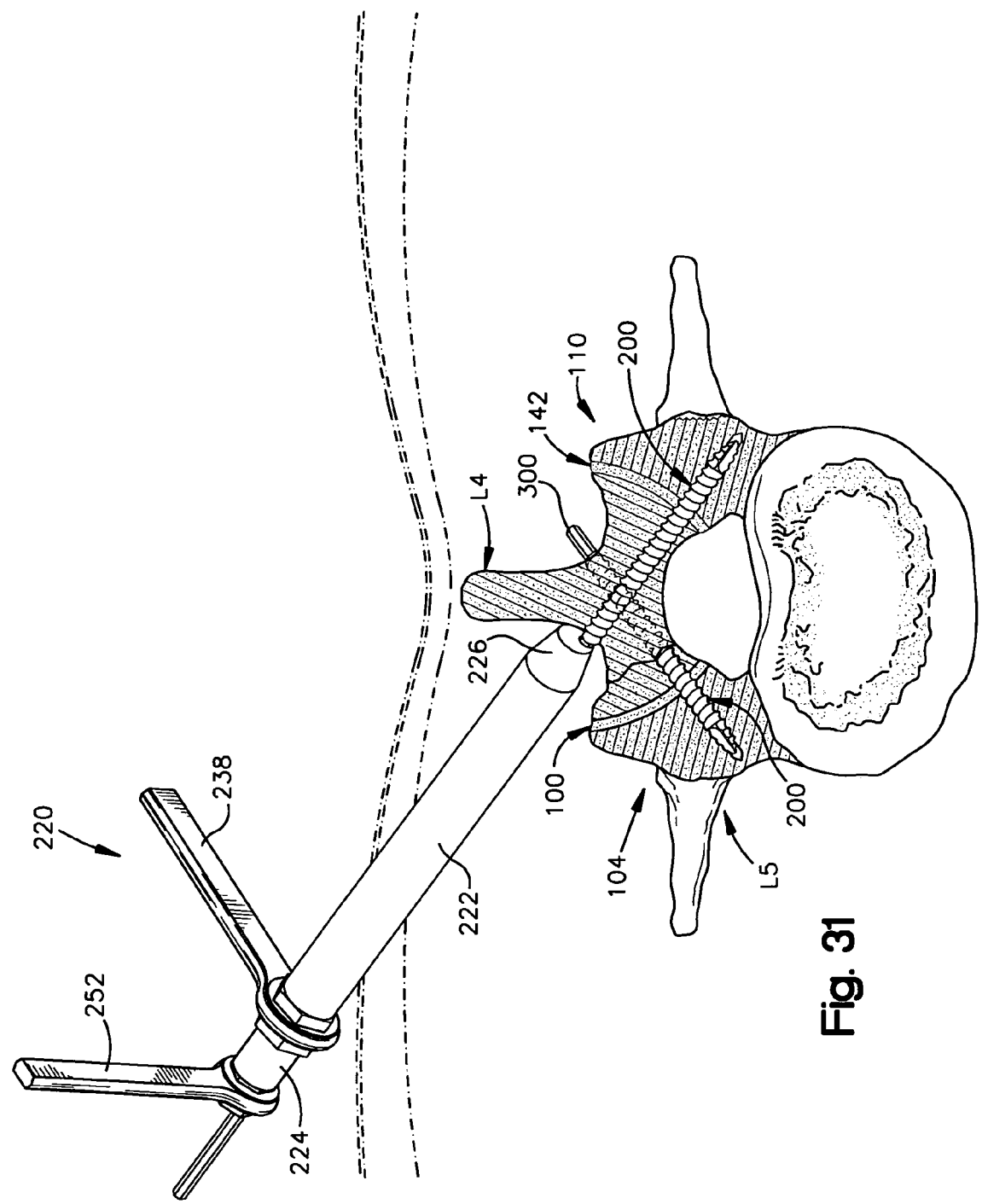

FIGS. 30 and 31 illustrate use of the tool 220 to shear off the majority of the shearable section 210 of each of the screws 200. With the second sleeve 224 disposed coaxially within the first sleeve 222, the passage 232 in the first sleeve is aligned with the shearing aperture 248 in the second sleeve. The tool 220 is then slid over the proximal end 204 of the first screw 200 and lowered through the incision in the skin 108 on the second side 110 of the vertebrae over the shearable section 210 of the screw until the distal end 226 of the first sleeve 222 contacts the L4 vertebrae. The first and second wrenches 238 and 252 are then placed on the first and second sleeves, respectively, and rotated relative to each other. The amount of relative rotation is small, but is done with sufficient force to cause the shearable section 210 to shear off at the junction of the offset passage 232 in the first sleeve is aligned with the offset shearing aperture 248 in the second sleeve. This shearing process creates an accessible head portion 300 (FIG. 31) of the screw 200 that lies above the surface of the lamina of the L4 vertebrae and has at a predetermined length of 8-12 mm that is defined by the axial length of the tapered nose section 230 at the distal end 226 of the first sleeve 222. FIG. 31 illustrates the aforementioned shearing step being done on the screw 200 that extends from the first side 104 of the vertebrae through the facet joint 100. It should be understood to those of ordinary skill in the art that the screws 200 need not be sheared off sequentially and could alternatively be sheared off immediately following their implantation.

Figure 32:
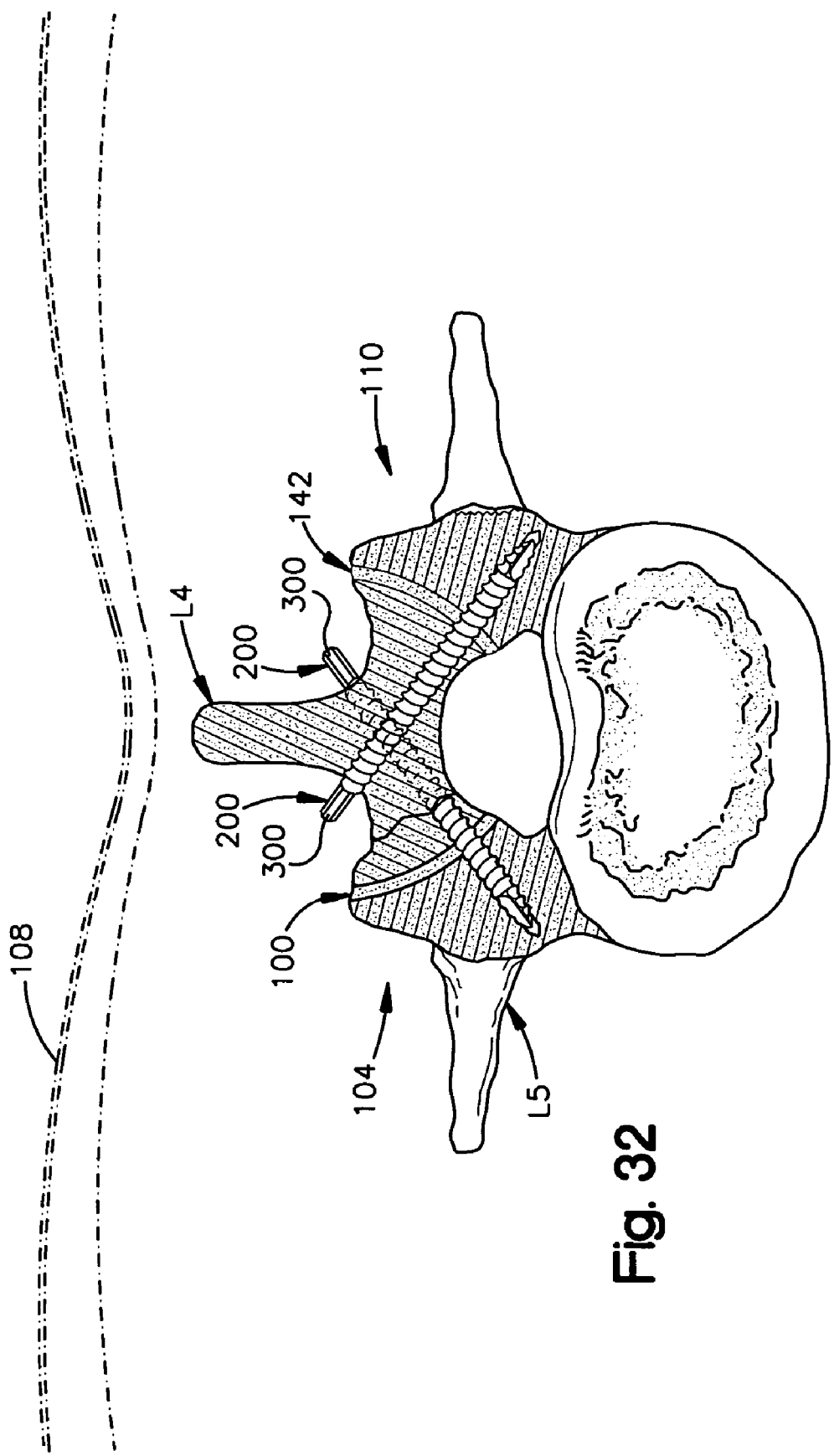

After the screws 200 have been sheared off to from the accessible head portions 300, the incisions are then closed. As shown in the completed view of FIG. 32, with the two screws 200 implanted across the facet joints 100 and 142 and the bone graft material 160 placed into both of the facet joints, fusion of the L4 and L5 vertebrae will take place over the next few months. FIG. 33 illustrates that the driving tool 400 can be used to remove the screws 200 at a later time after fusion of the facet joints 100 and 142 is achieved. The accessible head portions 300 of the screws 200 permits this removal to be accomplished in a minimally invasive manner.

It should be understood to those skilled in the art that the apparatus 10 could be used to implant screws for a variety using a transarticular (rather than translaminar) approach directly across the facet joints. Such an application could be accomplished by simply varying the placement of the K-wires 12 and 14 to achieve the necessary screw trajectories. It is contemplated that the implantation of transarticular screws may be best accomplished by inserting the first K-wire 12 into the lamina a few millimeters lateral of the spinous process rather than into the spinous process itself. It should be noted that the swivel block assembly 22 could be positioned between the fixation blocks 16 and 18 along the rod member 20 to aid with placement of direct (or transarticluar) facet screws.

The present invention described herein thus provides an apparatus and a minimally invasive method for placing screws either directly across the facet joints of adjacent vertebrae or indirectly across the facet joints through the lamina (i.e. translaminar) as both a primary means for spinal fixation and as a secondary means for fixation to augment anterior fusion or pedicle screw fixation instrumentation. It is contemplated that the apparatus could also be used to guide implantation for a variety of other orthopedic screws in the spine as well as other bones. Significantly, the present invention provides for the accurate and repeatable placement of facet screws and for fusing adjacent vertebrae in a minimally invasive procedure that saves time during surgery and is less traumatic to the patient.

From the above description of the invention, those skilled in the art will perceive improvements, changes and modifications. Such improvements, changes and modifications within the skill of the art are intended to be covered by the appended claims.

Having described the invention, I claim:

1. A minimally invasive surgical method for fusing adjacent upper and lower vertebrae, said method comprising the steps of:
    providing an apparatus comprising first and second K-wires, first and second fixation blocks, a swivel block having relatively movable first and second block members, a rod member extending between the fixation blocks and the first block member, and a cannula extending from the second block member;
    inserting the first K-wire into the spinous process of the upper vertebrae;
    inserting the second K-wire into the transverse process on a first side of the lower vertebrae;
    securing the first fixation block to the first K-wire and the second fixation block to the second K-wire with the rod member extending across the K-wires;
    securing the second block member of the swivel block assembly relative to the first block member to achieve a desired angle for a first axis along which a first screw will be implanted into the facet joint on the first side;
    securing the swivel block assembly at a desired axial position on the rod member;
    obtaining percutaneous access along the first axis to a second side of the upper vertebrae via the cannula;
    providing a first one removable screw for insertion into the cannula, the first screw having a threaded section for implantation across the facet joint to promote fusion of the adjacent vertebrae and an elongated shank section that is shearable subcutaneously following implantation;
    inserting the first screw through the cannula;
    implanting the threaded section of the first screw along the first axis across the facet joint on the first side to attach the upper and lower vertebrae;
    percutaneously inserting a shearing tool over the elongated shank section of the first screw; and
    shearing the elongated shank section of the first screw with the shearing tool to form an accessible head portion of the shank section that lies above the surface of the lamina of the upper vertebrae.

2. The method of claim 1 wherein prior to said step of securing the second block member of the swivel block assembly relative to the first block member to achieve a desired angle for the first axis, said method further comprising the steps of:
    moving the cannula to aim the cannula toward the facet joint on the second side of the vertebrae along a second axis;
    obtaining percutaneous access along the second axis to the facet joint on the second side via the cannula; and
    placing a bone graft material into the facet joint on the second side through the cannula to assist with fusion of the upper and lower vertebrae.

3. The method of claim 2 further comprising the steps of:
    inserting a burring bit into the cannula; and
    burring the articular surfaces of the facet joint on the second side to widen the said facet joint for accepting a bone graft material.

4. The method of claim 1 further comprising the steps of:
    removing the cannula from percutaneous insertion on the second side;
    removing the second K-wire from the transverse process on the first side of the lower vertebrae;
    inserting the second K-wire into the transverse process on the second side of the lower vertebrae;
    securing the second fixation block to the second K-wire;
    releasing the first fixation block from the first K-wire and rotating the first fixation block with the rod member extending across the K-wires;
    securing the first fixation block to the first K-wire;
    securing the second block member of the swivel block assembly relative to the first block member to achieve a desired angle for a third axis on which a second screw will be implanted into the facet joint on the second side;
    securing the swivel block assembly at a desired axial position along the rod member;
    obtaining percutaneous access to the first side of the upper vertebrae via the cannula;
    providing a second removable screw for insertion into the cannula, the second screw having a threaded section for implantation across the facet joint to promote fusion of the adjacent vertebrae and an elongated shank section that is shearable subcutaneously following implantation;
    inserting the second screw through the cannula;
    implanting the threaded section of the second screw along the third axis across the facet joint on the second side to attach the upper and lower vertebrae;
    percutaneously inserting the shearing tool over the elongated shank section of the second screw; and
    shearing the elongated shank section of the second screw with the shearing tool to form an accessible head portion of the shank section that lies above the surface of the lamina of the upper vertebrae.

5. The method of claim 4 further comprising the steps of:
moving the cannula to aim the cannula along a fourth axis toward the facet joint on the first side previously secured with the first screw;
obtaining percutaneous access to the facet joint on the first side via the cannula; and
placing a bone graft material through the cannula and into the facet joint on the first side around the previously implanted first screw to assist with fusion of the upper and lower vertebrae.

6. The method of claim 5 further comprising the steps of:
inserting a burring bit into the cannula; and
burring the articular surfaces of the facet joint on the first side to widen said facet joint around the first screw for accepting a bone graft material.

7. The method of claim 4 wherein said steps of shearing the first screw and shearing the second screw are completed consecutively.

8. The method of claim 4 wherein prior to said step of placing a bone graft material, said method further comprises the step of temporarily backing the threaded section of the first screw out of the facet joint on the first side of the vertebrae.

9. The method of claim 4 wherein said step of securing the second block member of the swivel block assembly relative to the first block member to achieve a desired angle for the third axis along which the second screw is implanted includes the step of calculating the desired angle for the centerline of the cannula to extend from the first side of the vertebrae toward the facet joint on the second side along the third axis.

10. The method of claim 4 wherein said step of securing the swivel block assembly at a desired axial position on the rod member includes the step of calculating the desired axial position for the swivel block assembly along the rod member.

11. The method of claim 4 wherein said step of securing the second block member of the swivel block assembly relative to the first block member to achieve a desired angle for the first axis along which the first screw is implanted includes the step of calculating the desired angle for the centerline of the cannula to extend from the second side of the vertebrae toward the facet joint on the first side along the first axis.

12. The method of claim 4 wherein said step of securing the swivel block assembly at a desired axial position on the rod member includes the step of calculating the desired axial position for the swivel block assembly along the rod member.

* * * * *